(12) United States Patent
Liu

(10) Patent No.: US 9,518,104 B2
(45) Date of Patent: Dec. 13, 2016

(54) COMPOSITIONS AND METHODS FOR TREATING MULTIPLE SCLEROSIS

(71) Applicant: Centre for Addiction and Mental Health, Toronto (CA)

(72) Inventor: Fang Liu, Toronto (CA)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 14/370,515

(22) PCT Filed: Jan. 4, 2013

(86) PCT No.: PCT/CA2013/000002
§ 371 (c)(1),
(2) Date: Jul. 3, 2014

(87) PCT Pub. No.: WO2013/102265
PCT Pub. Date: Jul. 11, 2013

(65) Prior Publication Data
US 2014/0378387 A1    Dec. 25, 2014

Related U.S. Application Data

(60) Provisional application No. 61/583,448, filed on Jan. 5, 2012.

(51) Int. Cl.
*C07K 14/705* (2006.01)
*A61K 38/00* (2006.01)

(52) U.S. Cl.
CPC ......... *C07K 14/70571* (2013.01); *A61K 38/00* (2013.01); *C07K 2319/00* (2013.01); *C07K 2319/10* (2013.01); *C07K 2319/23* (2013.01)

(58) Field of Classification Search
None
See application file for complete search history.

(56) References Cited

FOREIGN PATENT DOCUMENTS

WO    2008/025163    3/2008
WO    2013102264 A1    7/2013

OTHER PUBLICATIONS

Behan et al., The sad plight of multiple sclerosis research (low on fact, high on fiction): critical data to support it being a neurocristopathy, 2010, Inflammopharmacol 18:265-290.*
Groom et al., Multiple Sclerosis and Glutamate, 2003. Ann. N.Y. Acad. Sci. 993: 229-275.*
Ransohoff, R. M., Animal models of multiple sclerosis: the good, the bad and the bottom line, Aug. 2012, Nature Neuroscience 15(8):1074-1077.*
't Hart et al., Modelling of multiple sclerosis: lessons learned in a non-human primate, Oct. 2004, The Lancet Neurology 3:588-597.*
Wekerle et al., Animal models of multiple sclerosis, 2006, Drug Discovery Today: Disease Models 3(44):359-367.*
International Search Report received in PCT/CA2013/000002 mailed Mar. 19, 2013.
"Written Opinion received in PCT/CA2013/000002 mailed Mar. 19, 2013".
Boulter, et al., "Molecular Cloning and Functional Expression of Glutamate Receptor Subunit Genes", Aug. 31, 1990, pp. 1033-1037, vol. 249, No. 4972, Publisher: Science.
Wang, et al., "Direct interaction between GluR2 and GAPDH regulates AMPAR-mediated excitotoxicity", Apr. 26, 2012, pp. 1-12, vol. 5, No. 1, Publisher: Molecular Brain, Biomed Central Ltd.
Pitt, et al., "Glutamate Excitotoxicity in a Model of Multiple Slcerosis", Jan. 1, 2000, pp. 67-70, vol. 6, No. 1, Publisher: Nature Medicine, Nature Publishing Group.
Supplementary European Search Report received in EP 13733648, mailed Oct. 12, 2015.
Zhai, et al., "Disruption of the GluR2/GAPDH complex protects against ischemia-induced neuronal damage", Jan. 27, 2013, pp. 392-403, vol. 54, Publisher: Neurobiology of Disease, Blackwell Scientific Publications.
Zhai, et al., "Blocking GluR2-GAPDH ameliorates experimental autoimmune encephalomyelitis", Apr. 2015, pp. 388-400, vol. 2, No. 4, Publisher: Annals of Clinical and Translational Neurobiology.

* cited by examiner

*Primary Examiner* — John Ulm
(74) *Attorney, Agent, or Firm* — Suzannah K. Sundby, Esq.; Canady + Lortz LLP

(57) ABSTRACT

Disclosed are polypeptides, compositions and methods for the treatment or prophylaxis of multiple sclerosis. The method involves the steps of administering a polypeptide, or nucleic acid encoding the polypeptide, comprising the GluR2 NTa1-3-2 (Y142-K172) amino acid sequence as shown by SEQ ID NO:1 or SEQ ID NO:5 to a subject in need of the treatment.

21 Claims, 22 Drawing Sheets

FIGURE 1A: GluR2 NT1-3-2

YYQWDKFAYLYDSDRGLSTLQAVLDSAAEKK (SEQ ID NO:1)

FIGURE 1B: Fragment 1 (Tyr142 – Leu161) of GluR2 N-terminus
YYQWDKFAYLYDSDRGLSTL (SEQ ID NO:7)

FIGURE 1C : Fragment 2 (Asp153 – Lys172) of GluR2 N-terminus;
DSDRGLSTLQAVLDSAAEKK (SEQ ID NO:5)

FIGURE 1D:DNA sequence of GluR2 amino terminus:

1 atgcaaaaga ttatgcatat ttctgtcctc ctttctcctg ttttatgggg actgattttt
61 ggtgtctctt ctaacagcat acagataggg gggctatttc caaggggcgc tgatcaagaa
121 tacagtgcat ttcgggtagg gatggttcag ttttccactt cggagttcag actgacaccc
181 catatcgaca atttggaggt agccaacagt ttcgcagtca ccaatgcttt ctgctcccag
241 ttttcaagag gagtctacgc aattttttgga ttttatgaca agaagtctgt aaataccatc
301 acatcattct gtgggacact ccatgtgtcc ttcatcacac ctagcttccc aacagatggc
361 acacatccat ttgtcatcca gatgcgacct gacctcaaag gagcactcct tagcttgatt
421 <u>gagtactacc aatgggacaa gttcgcatac ctctatgaca gtgacagagg cttatcaaca</u>
481 <u>ctgcaagctg ttctggattc tgctgcagag aagaag</u>tggc aggtgactgc tatcaatgtg
541 gggaacatca acaatgacaa gaaagatgag acctacagat cgctctttca agatctggag
601 ttaaaaaaag aacggcgtgt aatcctggac tgtgaaaggg ataaagtaaa tgacattgtg
661 gaccaggtta ttaccattgg aaaacatgtt aaagggtacc attatatcat tgcaaatctg
721 ggattcactg atgggggacct gctgaaaatt cagtttggag gagcaaatgt ctctggatt
781 cagattgtag actacgatga ttccctggtg tctaaattta tagaaagatg gtcaacactg
841 gaagagaaag aatccctgg agcacacaca gcgacaatta agtatacttc ggccctgacg
901 tatgatgctg tccaagtgat gactgaagca ttccgtaacc ttcggaagca gaggattgaa
961 atatcccgga gaggaaatgc aggggattgt ttggccaacc cagctgtgcc ctgggggacaa
1021 ggggtcgaaa tagaaagggc cctcaagcag gttcaagttg aaggcctctc tggaaatata
1081 aagtttgacc agaatggaaa acgaataaac tacacaatta acatcatgga gctcaaaaca
1141 aatggacccc ggaagattgg gtactggagt gaagtggata aatggttgt caccctaact
1201 gagctcccat caggaaatga cacgtctggg cttgaaaaca agactgtggt ggtcaccaca
1261 atattggaat ctccatatgt tatgatgaag aaaaatcatg aaatgcttga agggaatgag
1321 cgttacgagg gctactgtgt tgacttagct gcagaaattg ccaaacactg tgggttcaag
1381 tacaagctga ctattgttgg ggatggcaag tatggggcca gggatgccga caccaaaatt
1441 tggaatggta tggttggaga gcttgtctac gggaaagctg acattgcaat tgctccatta
1501 actatcactc tcgtgagaga agaggtgatt gacttctcca agcccttcat gagtcttgga
1561 atctctatca tgatcaagaa gcctcagaag tccaaaccag gagtgttttc ctttctgat
1621 cctttagcct atgag (SEQ ID NO:2)

The shaded and underlined region shows a representative sequence encoding GluR2 NT1-3-2 (Y142-K172).

FIGURE 1E: V22-E545 of GluR2 (GluR2 NT1-3-2 is underlined)

GluR₂NT V₂₂-E₅₄₅

```
22          31          41          51
 VSSNSIQIG  GLFPRGADQE  YSAFRVGMVQ  FSTSEFRLTP
61          71          81          91
HIDNLEVANS  FAVTNAFCSQ  FSRGVYAIFG  FYDKKSVNTI
101         111         121         131
TSFCGTLHVS  FITPSFPTDG  THPFVIQMRP  DLKGALLSLI
141         151         161         171
EYYQWDKFAY  LYDSDRGLST  LQAVLDSAAE  KKWQVTAINV
181         191         201         211
GNINNDKKDE  TYRSLFQDLE  LKKERRVILD  CERDKVNDIV
221         231         241         251
DQVITIGKHV  KGYHYIIANL  GFTDGDLLKI  QFGGANVSGF
261         271         281         291
QIVDYDDSLV  SKFIERWSTL  EEKEYPGAHT  ATIKYTSALT
301         311         321         331
YDAVQVMTEA  FRNLRKQRIE  ISRRGNAGDC  LANPAVPWGQ
341         351         361         371
GVEIERALKQ  VQVEGLSGNI  KFDQNGKRIN  YTINIMELKT
381         391         401         411
NGPRKIGYWS  EVDKMVVTLT  ELPSGNDTSG  LENKTVVVTT
421         431         441         451
ILESPYVMMK  KNHEMLEGNE  RYEGYCVDLA  AEIAKHCGFK
461         471         481         491
YKLTIVGDGK  YGARDADTKI  WNGMVGELVY  GKADIAIAPL
501         511         521         531
TITLVREEVI  DFSKPFMSLG  ISIMIKKPQK  SKPGVFSFLD
541
PLAYE (SEQ ID NO:3)
```

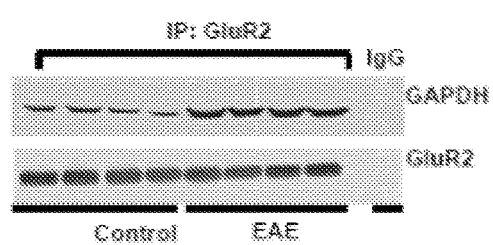
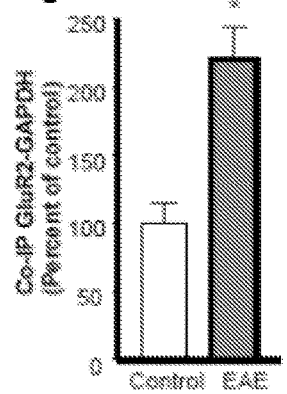
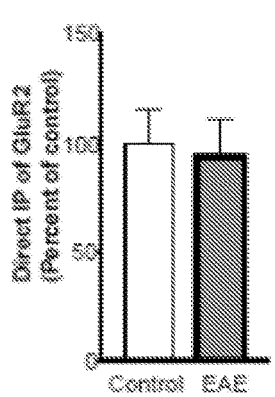
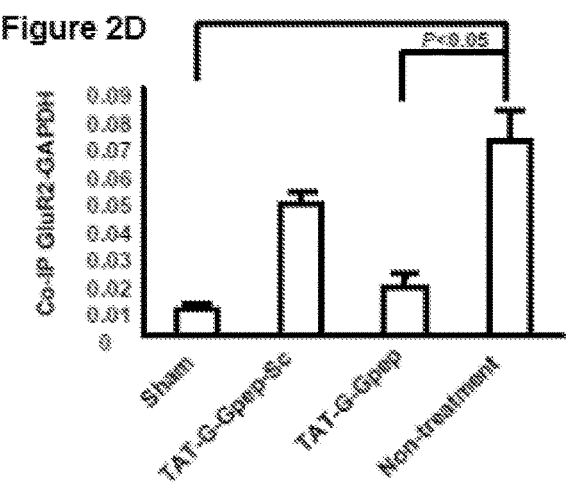

A
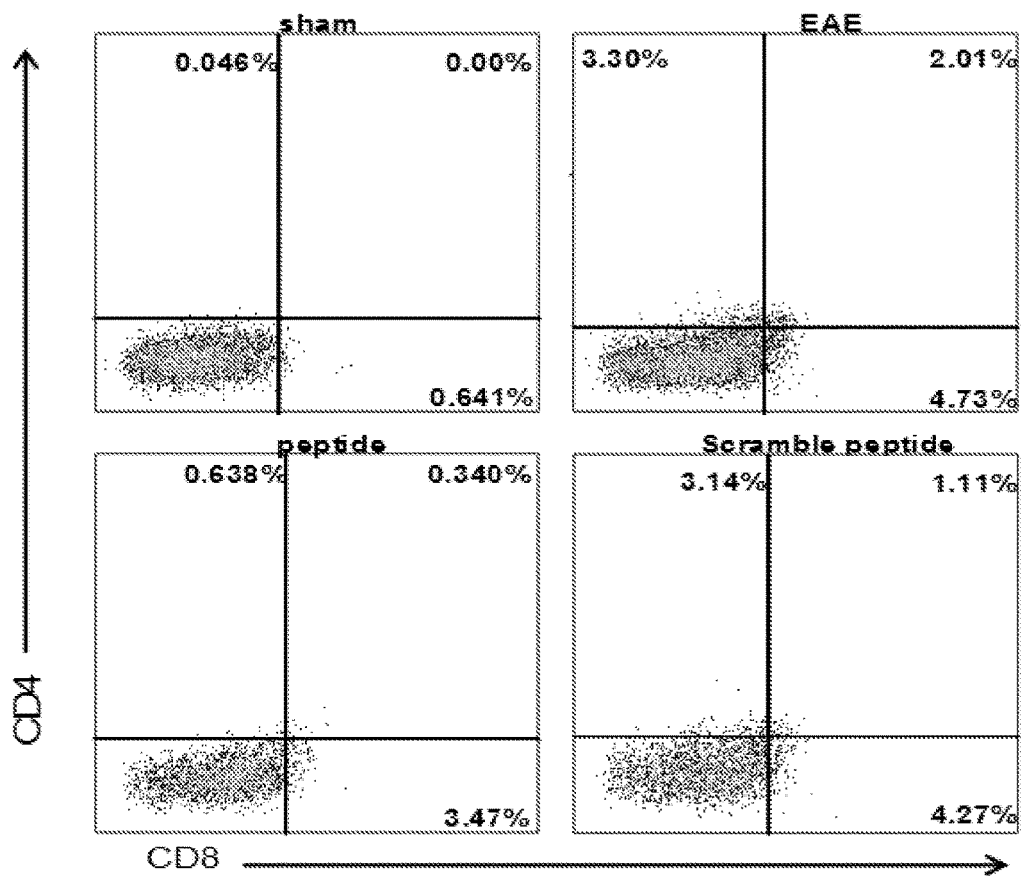
B
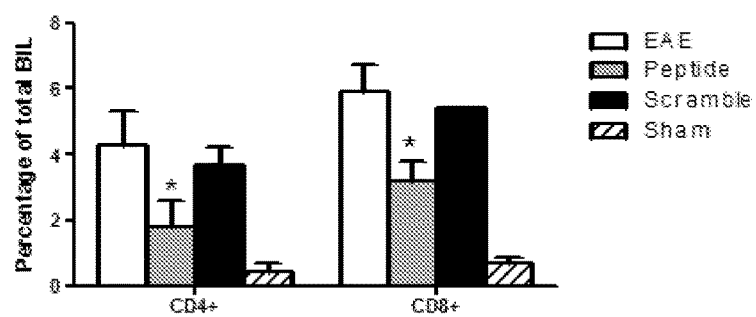
FIG. 16

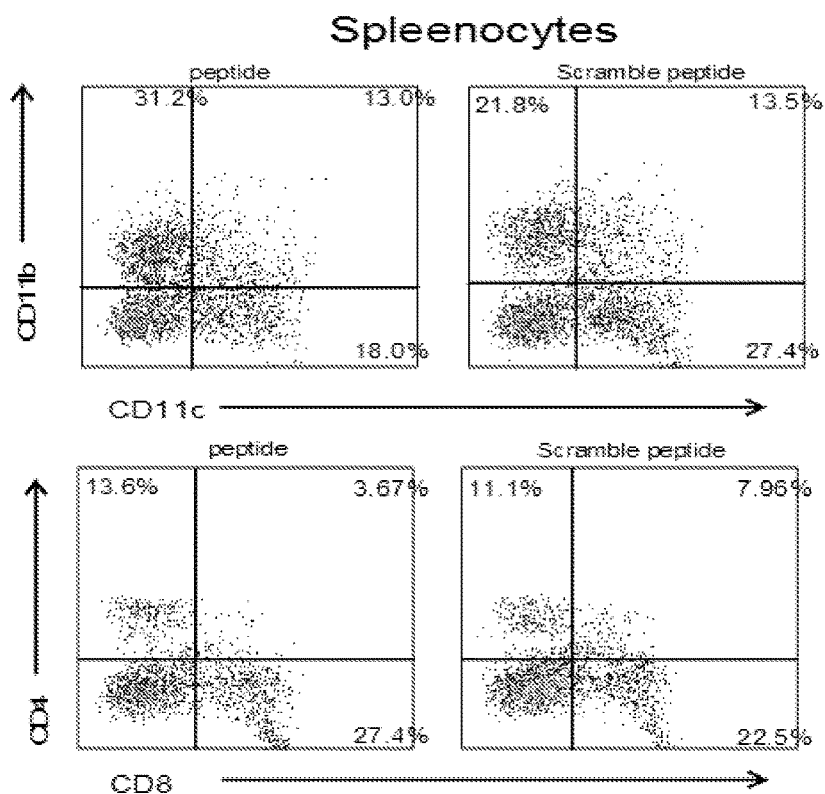
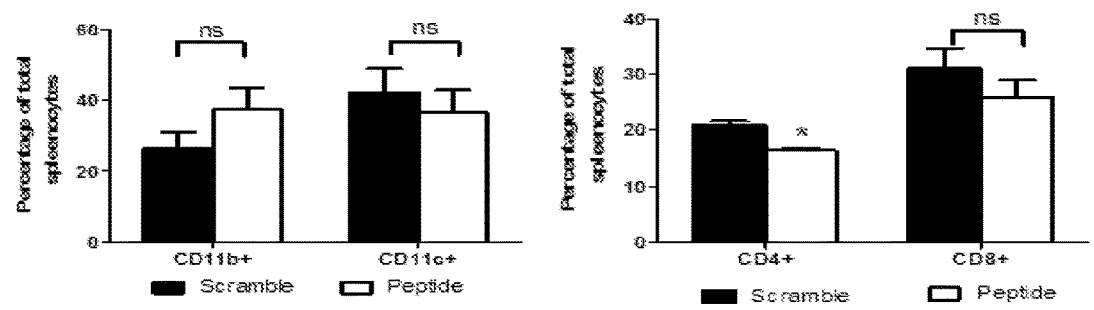
FIG. 17

SEQUENCE LISTING

<160> NUMBER OF SEQ ID NOS: 7

<210> SEQ ID NO 1
<211> LENGTH: 31
<212> TYPE: PRT
<213> ORGANISM: Artificial Sequence
<220> FEATURE:
<223> OTHER INFORMATION: GluR2 NT1-3-2

<400> SEQUENCE: 1

Tyr Tyr Gln Trp Asp Lys Phe Ala Tyr Leu Tyr Asp Ser Asp Arg Gly
1               5                   10                  15

Leu Ser Thr Leu Gln Ala Val Leu Asp Ser Ala Ala Glu Lys Lys
            20                  25                  30

<210> SEQ ID NO 2
<211> LENGTH: 1635
<212> TYPE: DNA
<213> ORGANISM: Artificial Sequence
<220> FEATURE:
<223> OTHER INFORMATION: DNA sequence of GluR2 amino terminus

<400> SEQUENCE: 2

```
atgcaaaaga ttatgcatat ttctgtcctc ctttctcctg ttttatgggg actgattttt      60
ggtgtctctt ctaacagcat acagataggg gggctatttc aaggggcgc tgatcaagaa     120
tacagtgcat tcgggtagg gatggttcag ttttccactt cggagttcag actgacaccc     180
catatcgaca atttggaggt agccaacagt tcgcagtcca ccaatgcttt ctgctcccag     240
ttttcaagag gagtctacgc aattttgga ttttatgaca agaagtctgt aaataccatc     300
acatcattct gtgggacact ccatgtgtcc ttcatcacac ctagcttccc aacagatggc     360
acacatccat tgtcatcca gatgcgacct gacctcaaag gagcactcct tagcttgatt     420
gagtactacc aatgggacaa gttcgcatac tctatgaca gtgacagagg cttatcaaca     480
ctgcaagctg ttctggattc tgctgcagag aagaagtggc aggtgactgc tatcaatgtg     540
gggaacatca caatgacaa gaaagatgag acctacagat cgctctttca agatctggag     600
ttaaaaaaag aacggcgtgt aatcctggac tgtgaaaggg ataaagtaaa tgacattgtg     660
gaccaggtta ttaccattgg aaaacatgtt aagggtacc attatatcat tgcaaatctg     720
ggattcactg atgggacct gctgaaaatt cagtttggag gagcaaatgt ctctggattt     780
cagattgtag actacgatga ttccctggtg tctaaattta agaaagatg gtcaacactg     840
gaagagaaag aatacccctgg agcacacaca gcgacaatta gtatacttc ggccctgacg     900
tatgatgctg tccaagtgat gactgaagca ttccgtaacc ttcggaagca gaggattgaa     960
atatcccgga gaggaaatgc aggggattgt ttggccaacc cagctgtgcc ctggggacaa    1020
ggggtcgaaa tagaaagggc cctcaagcag gttcaagttg aaggcctctc tggaaatata    1080
aagtttgacc agaatggaaa acgaataaac tacacaatta acatcatgga gctcaaaaca    1140
aatggaccc ggaagattgg gtactggagt gaagtggata aaatggttgt caccctaact    1200
gagctcccat caggaaatga cacgtctggg cttgaaaaca agactgtggt ggtcaccaca    1260
atattggaat ctccatatgt tatgatgaag aaaaatcatg aaatgcttga agggaatgag    1320
cgttacgagg gctactgtgt tgacttagct gcagaaattg ccaaacactg tgggttcaag    1380
tacaagctga ctattgttgg ggatggcaag tatggggcca gggatgccga caccaaaatt    1440
tggaatggta tggttggaga gcttgtctac gggaaagctg acattgcaat tgctccatta    1500
actatcactc tcgtgagaga agaggtgatt gacttctcca gcccttcat gagtcttgga    1560
atctctatca tgatcaagaa gcctcagaag tccaaaccag gagtgttttc ctttcttgat    1620
cctttagcct atgag                                                    1635
```

<210> SEQ ID NO 3
<211> LENGTH: 524
<212> TYPE: PRT
<213> ORGANISM: Artificial Sequence
<220> FEATURE:
<223> OTHER INFORMATION: V22-E545 of GluR2

<400> SEQUENCE: 3

```
Val Ser Ser Asn Ser Ile Gln Ile Gly Gly Leu Phe Pro Arg Gly Ala
1               5                   10                  15

Asp Gln Glu Tyr Ser Ala Phe Arg Val Gly Met Val Gln Phe Ser Thr
            20                  25                  30

Ser Glu Phe Arg Leu Thr Pro His Ile Asp Asn Leu Glu Val Ala Asn
        35                  40                  45

Ser Phe Ala Val Thr Asn Ala Phe Cys Ser Gln Phe Ser Arg Gly Val
    50                  55                  60

Tyr Ala Ile Phe Gly Phe Tyr Asp Lys Lys Ser Val Asn Thr Ile Thr
65                  70                  75                  80

Ser Phe Cys Gly Thr Leu His Val Ser Phe Ile Thr Pro Ser Phe Pro
                85                  90                  95

Thr Asp Gly Thr His Pro Phe Val Ile Gln Met Arg Pro Asp Leu Lys
            100                 105                 110

Gly Ala Leu Leu Ser Leu Ile Glu Tyr Tyr Gln Trp Asp Lys Phe Ala
        115                 120                 125

Tyr Leu Tyr Asp Ser Asp Arg Gly Leu Ser Thr Leu Gln Ala Val Leu
    130                 135                 140

Asp Ser Ala Ala Glu Lys Lys Trp Gln Val Thr Ala Ile Asn Val Gly
145                 150                 155                 160

Asn Ile Asn Asn Asp Lys Lys Asp Glu Thr Tyr Arg Ser Leu Phe Gln
                165                 170                 175

Asp Leu Glu Leu Lys Lys Glu Arg Arg Val Ile Leu Asp Cys Glu Arg
            180                 185                 190

Asp Lys Val Asn Asp Ile Val Asp Gln Val Ile Thr Ile Gly Lys His
        195                 200                 205

Val Lys Gly Tyr His Tyr Ile Ile Ala Asn Leu Gly Phe Thr Asp Gly
    210                 215                 220

Asp Leu Leu Lys Ile Gln Phe Gly Gly Ala Asn Val Ser Gly Phe Gln
225                 230                 235                 240

Ile Val Asp Tyr Asp Asp Ser Leu Val Ser Lys Phe Ile Glu Arg Trp
                245                 250                 255

Ser Thr Leu Glu Glu Lys Glu Tyr Pro Gly Ala His Thr Ala Thr Ile
            260                 265                 270

Lys Tyr Thr Ser Ala Leu Thr Tyr Asp Ala Val Gln Val Met Thr Glu
        275                 280                 285

Ala Phe Arg Asn Leu Arg Lys Gln Arg Ile Glu Ile Ser Arg Arg Gly
    290                 295                 300

Asn Ala Gly Asp Cys Leu Ala Asn Pro Ala Val Pro Trp Gly Gln Gly
305                 310                 315                 320

Val Glu Ile Glu Arg Ala Leu Lys Gln Val Gln Val Glu Gly Leu Ser
                325                 330                 335

Gly Asn Ile Lys Phe Asp Gln Asn Gly Lys Arg Ile Asn Tyr Thr Ile
            340                 345                 350

Asn Ile Met Glu Leu Lys Thr Asn Gly Pro Arg Lys Ile Gly Tyr Trp
        355                 360                 365

Ser Glu Val Asp Lys Met Val Val Thr Leu Thr Glu Leu Pro Ser Gly
    370                 375                 380

Asn Asp Thr Ser Gly Leu Glu Asn Lys Thr Val Val Val Thr Thr Ile
385                 390                 395                 400
```

```
Leu Glu Ser Pro Tyr Val Met Met Lys Lys Asn His Glu Met Leu Glu
                405                 410                 415
Gly Asn Glu Arg Tyr Glu Gly Tyr Cys Val Asp Leu Ala Ala Glu Ile
            420                 425                 430
Ala Lys His Cys Gly Phe Lys Tyr Lys Leu Thr Ile Val Gly Asp Gly
        435                 440                 445
Lys Tyr Gly Ala Arg Asp Ala Asp Thr Lys Ile Trp Asn Gly Met Val
    450                 455                 460
Gly Glu Leu Val Tyr Gly Lys Ala Asp Ile Ala Ile Ala Pro Leu Thr
465                 470                 475                 480
Ile Thr Leu Val Arg Glu Glu Val Ile Asp Phe Ser Lys Pro Phe Met
                485                 490                 495
Ser Leu Gly Ile Ser Ile Met Ile Lys Lys Pro Gln Lys Ser Lys Pro
            500                 505                 510
Gly Val Phe Ser Phe Leu Asp Pro Leu Ala Tyr Glu
        515                 520

<210> SEQ ID NO 4
<211> LENGTH: 41
<212> TYPE: PRT
<213> ORGANISM: Artificial Sequence
<220> FEATURE:
<223> OTHER INFORMATION: G-Gpep-sc or G-Gpep-scrambled

<400> SEQUENCE: 4

Tyr Gly Arg Lys Lys Arg Arg Gln Arg Arg Ala Phe Asp Leu Ser
1               5                   10                  15

Gln Tyr Asp Leu Lys Trp Gln Val Asp Tyr Leu Lys Tyr Asp Tyr Gly
            20                  25                  30

Thr Ala Ser Glu Leu Arg Ala Ser Ala
        35                  40

<210> SEQ ID NO 5
<211> LENGTH: 20
<212> TYPE: PRT
<213> ORGANISM: Artificial Sequence
<220> FEATURE:
<223> OTHER INFORMATION: Fragment 2 (Asp153 - Lys172) of GluR2
      N-terminus

<400> SEQUENCE: 5

Asp Ser Asp Arg Gly Leu Ser Thr Leu Gln Ala Val Leu Asp Ser Ala
1               5                   10                  15

Ala Glu Lys Lys
            20

<210> SEQ ID NO 6
<211> LENGTH: 21
<212> TYPE: PRT
<213> ORGANISM: Artificial Sequence
<220> FEATURE:
<223> OTHER INFORMATION: (MOG) peptide 35-55

<400> SEQUENCE: 6

Met Glu Val Gly Trp Tyr Arg Ser Pro Phe Ser Arg Val Val His Leu
1               5                   10                  15

Tyr Arg Asn Gly Lys
            20

<210> SEQ ID NO 7
```

```
<211> LENGTH: 20
<212> TYPE: PRT
<213> ORGANISM: Artificial Sequence
<220> FEATURE:
<223> OTHER INFORMATION: Fragment 1 (Tyr142 - Leu161) of GluR2
      N-terminus

<400> SEQUENCE: 7

Tyr Tyr Gln Trp Asp Lys Phe Ala Tyr Leu Tyr Asp Ser Asp Arg Gly
1               5                   10                  15

Leu Ser Thr Leu
            20
```

COMPOSITIONS AND METHODS FOR TREATING MULTIPLE SCLEROSIS

FIELD OF THE INVENTION

The present invention generally relates to polypeptides. The present invention also relates to polypeptides, compositions and methods for treatment or prophylaxis of a neurological condition. More specifically, the present invention relates to polyeptides, compositions and methods for treating multiple sclerosis.

BACKGROUND OF THE INVENTION

Multiple sclerosis (MS) is a demyelinating disease affecting the central nervous system, in which episodes of inflammation result in a highly variable course and progression of symptoms (Compston, A. & Coles, A., *Lancet* 372, 1502-1517, 2008). Onset is typically between the ages of 30-50, with higher prevalence in women and great geographic variability (Rosati, G., *Neurol Sci* 22, 117-139, 2001). There are a broad range of symptoms, reflecting the diverse anatomical targets of demyelination, but typical syndromes include: weakness, fatigue, loss of vision, cognitive impairment and impaired balance and coordination (Compston, supra). MS episodes are erratic in timing as well, leading to the general principle that MS lesions are disseminated in both space (location) and time (Adams, R et al., *Principles of Neurology*. sixth edn, (McGraw-Hill, 1997)). These symptoms can often be sufficient to make the diagnosis of MS, but magnetic resonance imaging (MRI) is also helpful, along with analysis of cerebrospinal fluid and nerve evoked potential measurements. MS typically begins with reversible neurological deficits (relapsing-remitting phase, or RRMS), that progress eventually to fixed disability in later life (secondary progressive phase)(Adams et al., supra). Like other aspects of the disease, the pattern, severity and timing of this progression can be very different among patients, with some experiencing profound disability with rapid progression at the outset (primary progressive MS or PPMS), while a small number of other patients have isolated, relatively mild symptoms.

The cause of MS is not known with certainty, but both genetic and environmental factors can affect susceptibility (Giovannoni, G. & Ebers, G., *Curr Opin Neurol* 20, 261-268, 2007). Prominent candidate genes include HLA DRB1 and DQB, which encode part of the human major histocompatibility complex (MHC), apolipoprotein E (APOE) and interferon gamma (IFN-g)(Giovannoni et al., supra; Kantarci, O. & Wingerchuk, D., *Curr Opin Neurol* 19, 248-254, 2006) The most commonly implicated environmental factors are vitamin D/sunlight, and infectious agents (including the Epstein-Barr virus, human endogenous retroviruses or HERV, and human herpesvirus-6 or HHV-6)(Giovannoni et al., supra). Although inflammation has been associated with MS, it is unclear whether demyelination is caused by a primary immune process or a neurodegenerative mechanism (Trapp, B. D. & Nave, K. A., *Annu Rev Neurosci* 31, 247-269, 2008). Autoimmune mechanisms in MS have been studied in depth, with CD4+ type 1 helper T-cells having been considered the main effector of the demyelination. Recently, other immune system components have also been implicated, suggesting that a more broad range of leukocytes may be involved, targeting both the myelin sheath and the axons themselves (Hemmer, B., et al., *Nat Rev Neurosci* 3, 291-301, 2002; Smith, T., et al., *Nat Med* 6, 62-66, 2000).

There is currently no cure for MS, and despite some recent progress in novel treatments, the disease remains a significant therapeutic challenge (Kieseier, B. C., et al., *Curr Opin Neurol* 20, 286-293, 2007). Standard treatment includes corticosteroids aimed at suppressing the inflammatory response during acute relapse, sometimes with plasmaphoresis to remove circulating antibodies from the bloodstream (Giovannoni et al., supra). Glatiramer acetate and interferon-β-1a are also used in RRMS, but are not particularly effective in PPMS, nor in altering the eventual course of MS, even with early intervention (Compston et al., supra; Kieseier et al., supra). A more specific immunotherapy uses monoclonal antibodies to target particular surface molecules involved in MS. Natalizumab binds to α4 integrin on white blood cells, thereby reducing their numbers, but due to adverse reactions of progressive multifocal leukoencephalopathy (PML), this drug is used only when other treatments have failed (Kieseier et al., supra). Other monoclonal antibodies, rituximab (an anti-CD20 antibody) and daclizumab (targeting CD-25), have a similar rationale, but again are not curative, and have other immunological side-effects.

The most common rodent model of MS consists of injecting myelin oligdendrocyte glycoprotein (MOG) to generate an autoimmune encephalitis (EAE). The EAE model exhibits an increase in mGluR5 expression in combination with decreased mGluR1a receptors in cerebellar Purkinje neurons. Treatment of EAE mice with an mGluR5 enhancer (RO0711401) improves motor coordination, but mGluR5 antagonists do not (Fazio, F. et al. *Neuropharmacology* 55, 491-499, 2008). EAE mice also show a transient reduction of $Ca^{++}$-dependent glutamate release from cerebral cortex synaptosomes, soon after the onset of the clinical signs (Vilcaes, A. A., et al., *J Neurochem* 108, 881-890, 2009). At the same time, the EAE elevates mRNA levels of the glutamate transporters GLT-1 and GLAST in forebrain and cerebellum, in conjunction with the elevation in extracellular glutamate, although protein levels of these transporters are not consistent with the mRNA findings (Mitosek-Szewczyk, K., et al., *Neuroscience* 155, 45-52, 2008). Other animal models of MS, such as the CNTF −/− mouse, have decreased glutamate decarboxylase, among several proteins in the altered in EAE (Linker, R. A. et al., *PLoS One* 4, e7624, 2009). The neurological effects of EAE can also be attenuated by the gap junction blocker carbenoxolone or the glutaminase inhibitor DON (6-diazo-5-oxo-L-norleucine), likely through decreased glutamate release from microglia (Shijie, J. et al. *Tohoku J Exp Med* 217, 87-92 (2009). In vitro activation of microglial mGluR2 exacerbates myelin-induced toxicity, while mGluR3 and group III mGluRs activation is protective (Pinteaux-Jones, F. et al., *J Neurochem* 106, 442-454, 2008).

The role of glutamate in excitotoxicity is well established, but there is evidence that this neurotransmitter system can also modulate immune system function, and may therefore be a novel therapeutic target for inflammatory disorders of the nervous system (Hansen, A. M. & Caspi, R. R. *Nat Med* 16, 856-858, 2010). Glutamatergic excitotoxicity may also be involved in the mechanisms of neuronal damage by inflammation, since activated immune cells release glutamate (Pitt, D., et al., *Nat Med* 6, 67-70, 2000; Groom, A. J., et al., *Ann N Y Acad Sci* 993, 229-275; discussion 287-228, 2003). Decreased expression of glutamate transporters EAAT (excitatory amino acid transporter) 1 and 2 was reported in post-mortem cerebral cortex samples from patients with MS. These changes correlated with the presence of microglial infiltration and demyelination (Vercellino, M. et al., *J Neuropathol Exp Neurol* 66, 732-739, 2007). Glutamate transporters EAAT-1 and -2 are expressed by oligodendrocytes, the myelin-producing cells, and in MS lesions, the expression of these transporters is lost (Pitt, D., et al., *Neurology* 61, 1113-1120, 2003). Both glutamate and AMPA can enhance T-lymphocyte proliferation in response to MOG and MBP (myelin basic protein) exposure, and mGluR3 mRNA and protein are elevated on T-lymphocytes from patients with active MS compared to controls (Sarchielli, P. et al., *J Neuroimmunol* 188, 146-158, 2007). Antibodies against NMDA receptors have been detected in a case of recurrent optic neuritis with transient cerebral lesions, in both serum and cerebrospinal fluid, further supporting the hypothesis that autoantibodies against glutamate receptors in the CNS may play a role in demyelinating diseases (Ishikawa, N., et al., Neuropediatrics 38, 257-260, 2007).

Excessive glutamate, acting mainly through NMDARs and AMPARs, facilitates $Ca^{2+}$ influx, which can result in excitotoxicity under pathological conditions including ischemia, trauma, hypoglycemia and epileptic seizure (Simon, R. P., et al., *Science* 226, 850-852, 1984; Choi, D. W. *Trends Neurosci.* 18, 58-60, 1995). The inhibition of Ca(2+)-permeable AMPA receptors may be of benefit in MS, based on the observation that mice with Gria3 mutations that do not express functional GluR3 AMPA receptor subunits, are resistant to demyelination and neurological sequelae in the EAE model (Bannerman, P. et al., *J Neurochem* 102, 1064-1070, 2007). In contrast, mGluR4 knockout mice are more vulnerable to the EAE model, with more T-helper cells becoming the $T_{H17}$ type that produce interleukin-17 (Fallarino, F. et al., Nat Med 16, 897-902, 2010). Treatment with a selective mGluR4 enhancer appears to be protective against EAE through enhancement of regulatory $T_{reg}$ cells (Fallarino et al., supra). The AMPAR subunit GluR1 forms a complex with the interferon-gamma (IFN-γ) receptor that, upon activation by IFN-γ, induces cytotoxicity (Mizuno, T. et al., *FASEB J* 22, 1797-1806, 2008). Direct application of AMPA/kainite antagonists NBQX or MPQX reduces the acute and chronic neurological effects of EAE in rats (Smith et al., supra). The protective effects of these drugs may not involve immunological mechanisms, since NBQX did not reduce the amount of inflammation or the in vitro proliferation of activated T-cells (Pitt et al., supra). AMPA-mediated excitotoxity has also been implicated in other neurodegerative disorders, such as ALS (amyotrophic lateral sclerosis), in which motor neurons are primarily affected. Editing of the GluR2 mRNA is altered in spinal motor neurons from patients with ALS, leading to a higher proportion of Q/R site-unedited GluR-containing $Ca^{++}$ permeable AMPA receptors Kwak, S., et al., *Neuropathology* 30, 182-188, 2010).

Functional changes in AMPARs are most often attributed to phosphorylation events mediated by cyclic AMP-dependent protein kinase (PKA), protein kinase C (PKC) and CaM kinase II (calcium-calmodulin kinase II)(Greengard, P., et al., *Science* 253, 1135-8, 1991; Wang, L. Y., et al., *J Physiol* 475, 431-7, 1994; Yakel, J. L., et al., Proc Natl Acad Sci USA 92, 1376-80, 1995; Soderling, T. R., *Biochim Biophys Acta* 1297, 131-8, 1996; Barria, A., et al., *J Biol Chem* 272, 32727-30, 1997). Recently, a variety of intracellular proteins have been reported to bind directly to AMPARs (Xia, J., et al., *Neuron* 22, 179-87, 1999; Dong, H., et al., *Nature* 386, 279-84, 1997; Osten, P., et al., *Neuron* 21, 99-110, 1998; Daw, M. I., et al., *Neuron* 28, 873-86, 2000; Allison, D. W., et al., *J Neurosci* 18, 2423-36, 1998). These proteins play important roles not only in receptor targeting or clustering, but also in the modulation of receptor activity and activation of signaling pathways. Protein-protein interactions have been shown to affect AMPAR trafficking and function. The best characterized AMPAR interacting proteins are those that interact with the intracellular carboxyl terminus (CT) of AMPAR subunits such as GRIP (Glutamate Receptor Interacting Protein), ABP (AMPAR-binding protein), SAP97 (synapse-associated protein-97), PICK1 (Protein interacting with C kinase-1), stargazin, NSF (N-ethylmaleimide-sensitive factor), and AP2 (adaptor protein-2)(Xia et al., supra; Dong et al., supra; Osten et al., supra; Daw et al., supra; Chen, L., et al., *Nature,* 408(6815), 936-43, 2000; Lee, S. H., et al., *Neuron,* 36(4): 661-74, 2002; Nishimune, A., et al., *Neuron,* 21(1): 87-97, 1998; Song, I., et al., *Neuron,* 21(2): 393-400, 1998; Srivastava, S., et al., Neuron, 21(3): 581-91, 1998; Dong, H., et al., *J Neurosci,* 19(16): 6930-41, 1999). These proteins have been shown to regulate AMPAR function in a variety of ways, including altering AMPAR localization, clustering and/or trafficking.

GAPDH is a tetrameric protein composed of four identical subunits (37 kDa). Each monomer has binding sites for the substrate (glyceraldehyde-3-phosphate, G3P) and the co-factor nicotinamide adenine dinucleotide ($NAD^+$)(Chuang, D. M., et al., *Annu Rev Pharmacol Toxicol* 45, 269-290, 2005; Sirover, M. A., *J Cell Biochem* 95, 45-52, 2005). Traditionally, GAPDH has been considered the key enzyme in glycolysis, and therefore, an important protein in energy production. In addition, GADPH was thought to be a housekeeping gene whose transcript level remained constant under most experimental conditions. However, recent evidence supports the notion that GAPDH plays a critical role in apoptosis, as indicated by changes in GAPDH expression and subcellular localization (Sawa, A., et al., *Proc Natl Acad Sci USA,* 94(21): p. 11669-74, 1997; Ishitani, R., et al., *Mol Pharmacol,* 53(4): p. 701-7, 1998; Ishitani, R. and D. M. Chuang, *Proc Natl Acad Sci USA,* 93(18): 9937-41, 1996; Hara, M. R., et al., *Nat Cell Biol,* 2005. 7(7): 665-74, 2005). GAPDH is overexpressed and accumulates in the nucleus during apoptosis induced by a variety of insults. The mechanism underlying GAPDH nuclear translocation and subsequent cell death remains largely unknown. However, recent studies have implicated several potential factors that may be involved in the process: (1) the expression of GAPDH is regulated by p53, a tumor suppressor protein and proapoptotic transcription factor, which suggests that GAPDH could be a downstream apoptotic mediator (Chen, R. W., et al., *J Neurosci* 19, 9654-9662, 1999); (2) overexpression of Bcl-2 blocks the apoptotic insults triggered by GAPDH overexpression, nuclear translocation and subsequent apoptosis, suggesting that Bcl-2 may participate in the regulation of GAPDH nuclear translocation, consistent with the anti-apoptic function of Bcl-2 (Dastoor, Z., and Dreyer, J. L., *J Cell Sci* 114, 1643-1653, 2001); (3) GAPDH binds to a nuclear localization-signal-containing protein, Siah1, which initiates its translocation to the nucleus. The association with GAPDH stabilizes Siah1 and thereby enhances Siah1-mediated proteolytic cleavage of its nuclear substrates and triggers apoptosis (Hara et al., supra; Hara, M. R., and Snyder, S. H., *Annu Rev Pharmacol Toxicol.,* 2006; Hara, M. R., and Snyder, S. H., *Cell Mol Neurobiol.,* 2006; Hara, M. R., et al., *Proc Natl Acad Sci USA* 103, 3887-3889, 2006).

Based on the foregoing, there is a need in the art for compositions and methods for the treatment and prophylaxis of MS.

SUMMARY OF THE INVENTION

The present invention relates to compositions and methods for treatment and prophylaxis of MS.

According to a first aspect of an embodiment of the invention there is provided a polypeptide comprising SEQ ID NO:5. In a second aspect of a separate embodiment, the polypeptide does not comprise SEQ ID NO:1. In a third aspect of a separate embodiment, the polypeptide does not comprise a naturally occurring GluR2 subunit, for example, naturally occuring in the genome or proteome of any animal or subject that has not been genetically manipulated by man.

According to an aspect of the present invention there is provided a polypeptide defined by a fragment of SEQ ID NO:1 that comprises 20 or more consecutive amino-acids thereof. For example, the polypeptide may comprise a fragment of SEQ ID NO:1 which comprises 20, 21, 22, 23, 24, 25, 26, 27, 28, 29, or 30 consecutive amino acids of SEQ ID NO:1. According to a further aspect, there is provided a polypeptide that is at least 80 identical in sequence to any one of the above, for example, 81%, 82%, 83%, 84%, 85%, 86%, 87%, 88%, 89%, 90%, 91%, 92%, 93%, 94%, 95%, 96%, 97%, 98% or 99%. Compositions that comprise the polypeptide as described above are also contemplated.

According to a further aspect of the present invention, there is provided a polypeptide comprising DSDRGLSTLQAVLDSAAEKK (SEQ ID NO:5) and wherein the polypeptide does not comprise SEQ ID NO:1.

In a further embodiment, the polypeptide comprises DSDRGLSTLQAVLDSAAEKK (SEQ ID NO:5), and is between 20 and 200 amino acids in length, for example, 20, 21, 22, 23, 24, 25, 26, 27, 28, 29, 30, 31, 32, 33, 34, 35, 36, 37, 38, 39, 40, 41, 42, 43, 44, 45, 46, 46, 48, 49, 50, 60, 70, 80, 90, 100, 110, 120, 130, 140, 150, 160, 170, 180, 190, 200 or more amino acids in length. The polypeptide may further comprise a range of lengths defined by any two values listed above, or any two values that lies between those specifically disclosed herein. Representative examples include, but without wishing to be considered limiting in any manner, 84 amino acids or a range of 21 to 157 amino acids.

In still a further embodiment, the polypeptide comprises DSDRGLSTLQAVLDSAAEKK (SEQ ID NO:5), but does not comprise SEQ ID NO:1 or a fragment thereof, for example, any 30, 29, 28, 27, 26, 25, 24, 23, 22, 21, 20, 19, 18, 17, 16, 15, 14, 13, 12, 11, 10, 9, 8, 7, 6, 5 or 4 consecutive amino acids defined in SEQ ID NO:1.

In a further embodiment, which is not meant to be limiting, the polypeptide comprises SEQ ID NO:5 but the C-terminal does not further comprise, in alternate embodiments, the amino acid defined by the one letter code A, R, N, D, B, C, E, Q, Z, G, H, I, L, K, M, F, P, S, T, W, Y or V. In still a further embodiment, which is not meant to be limiting in any manner the polypeptide comprises SEQ ID NO:5 but the N-terminal does not further comprise, in alternate separate embodiments, the amino acid defined by the one letter code A, R, N, D, B, C, E, Q, Z, G, H, I, L, K, M, F, P, S, T, W, Y or V. In yet a further embodiment, which is not meant to be limiting in any manner, the polypeptide comprises SEQ ID NO:5 but the N-terminal and C-terminal do not further each comprise individually, in alternate separate embodiments, an amino acid defined by the one letter code A, R, N, D, B, C, E, Q, Z, G, H, I, L, K, M, F, P, S, T, W, Y or V. Also contemplated are occasions where the polypeptide C-terminus +2, +3, +4, +5, additional amino acids and/or the N-terminus +2, +3, +4, +5 additional amino acids in addition to SEQ ID NO:5 adhere to the above restrictions.

Also contemplated herein are polypeptides that not identical to any GluR2 subunit that occurs in nature.

According to an aspect of the present invention, there is provided a method for treatment or prophylaxis of multiple sclerosis in a subject, comprising administering a polypeptide as defined above to a subject.

According to an another aspect of the present invention, there is provided a method for treatment or prophylaxis of multiple sclerosis in a subject, comprising administering a composition comprising the polypeptide as described to a subject.

According to a further aspect of the present invention, there is provided a method of increasing neuronal survival in a subject having multiple sclerosis, comprising administering a polypeptide as described above to a subject.

According to a yet further aspect of the present invention, there is provided a method of increasing neuronal survival in a subject having multiple sclerosis, comprising administering a composition comprising the polypeptide as described above to a subject.

According to an aspect of the present invention, there is provided a method for treatment or prophylaxis of multiple sclerosis in a subject, comprising administering a polypeptide of between 20 and 200 amino acids comprising a GluR2 NT1-3-2 (Y142-K172) amino acid sequence defined by SEQ ID NO:1 or SEQ ID NO:5 to a subject.

According to an another aspect of the present invention, there is provided a method for treatment or prophylaxis of multiple sclerosis in a subject, comprising administering a composition comprising polypeptide of between 20 and 200 amino acids comprising a GluR2 NT1-3-2 (Y142-K172) amino acid sequence defined by SEQ ID NO:1 or SEQ ID NO:5 to a subject.

According to a further aspect of the present invention, there is provided a method of increasing neuronal survival in a subject having multiple sclerosis, comprising administering a polypeptide of between 20 and 200 amino acids comprising a GluR2 NT1-3-2 (Y142-K172) amino acid sequence defined by SEQ ID NO:1 or SEQ ID NO:5 to a subject.

According to a yet further aspect of the present invention, there is provided a method of increasing neuronal survival in a subject having multiple sclerosis, comprising administering a composition comprising a polypeptide of between 20 and 200 amino acids comprising a GluR2 NT1-3-2 (Y142-K172) amino acid sequence defined by SEQ ID NO:1 or SEQ ID NO:5 to a subject.

In a non-limiting embodiment of the invention, the polypeptide consists of SEQ ID NO:1 or SEQ ID NO:5. In a further non-limiting embodiment, the polypeptide is a fusion protein that comprises a protein transduction domain, for example, but not limited to the TAT sequence as is known in the art. In embodiments wherein SEQ ID NO:1 or SEQ ID NO:5 are fused to a non-GluR2 subunit sequence (for example, a heterologous amino acid sequence) the fusion protein may be of any length provided it exhibits at least one desired activity as described herein.

The present invention also provides a polypeptide as defined above, that is attached covalently or non-covalently to a non-protein substrate, non-protein molecule, non-protein macromolecule, a support, or any combination thereof. Further, the polypeptide, non-protein substrate, non-protein molecule, non-protein macromolecule, support or any combination thereof may be labelled by an appropriate group or marker as is known in the art and as described herein.

In an embodiment of the method of the present invention, the subject is a mammal. Preferably, the mammal is a primate, and more preferably, the primate is a human.

It is to be noted that the present invention also contemplates additional uses for the peptides as described herein and throughout.

BRIEF DESCRIPTION OF THE DRAWINGS

These and other features of the invention will become more apparent from the following description in which reference is made to the appended drawings wherein:

FIG. 1, Panels A-E, shows nucleotide and amino acid sequences of polypeptides and nucleic as described herein. Panel A shows the GluR2 NT1-3-2 (Y142-K172) amino acid sequence (SEQ ID NO:1). Panel B shows the amino acid sequence of Fragment 1 (Tyr142-Leu161) of the GluR2 N-terminus (SEQ ID NO:7). Panel C shows the amino acid sequence of Fragment 2 (Asp153-Lys172) of GluR2 N-terminus (SEQ ID NO:5). Panel D shows a representative nucleotide sequence encoding a polypeptide that comprises the GluR2 NT1-3-2 (Y142-K172) amino acid sequence (SEQ ID NO:2). The shaded and underlined regions show a nucleotide sequence encoding residues Y142 to K172. Panel E shows a polypeptide sequence of GluR2 comprising V22 to E545 (SEQ ID NO:3). The GluR2 NT1-3-2 (Y142-K172) amino acid sequence is underlined.

FIG. 16, Panels A-B, shows results suggesting TAT-GluR2nt1-3-2 peptide but not the TAT-GluR2nt 1-3-2-scrm could block the infiltration of leukocytes into the CNS. Panel A, Representative FACS analysis of the BIL staining with CD4 and CD8. Panel B, Bar graph summarizing the FACS analysis of BIL in different groups. (*P<0.05, comparing with other groups, ANOVA, post hoc SNK test).

FIG. 17, Panels A-B, shows results suggesting TAT-GluR2nt1-3-2 peptide but not the TAT-GluR2nt 1-3-2-scrm could inhibit number of CD4+ and CD8+ cells but not the CD11b+ and CD11c+ in spleenocytes. Panel A, Representative FACS analysis of the BIL staining with CD4 and CD8. Panel B, Bar graph summarizing the FACS analysis of CD4/CD8, CD11b/CD11c in different groups. (*P<0.05, comparing with other groups, ANOVA, post hoc SNK test; ns, non-significant).

DETAILED DESCRIPTION

Figure 2E:
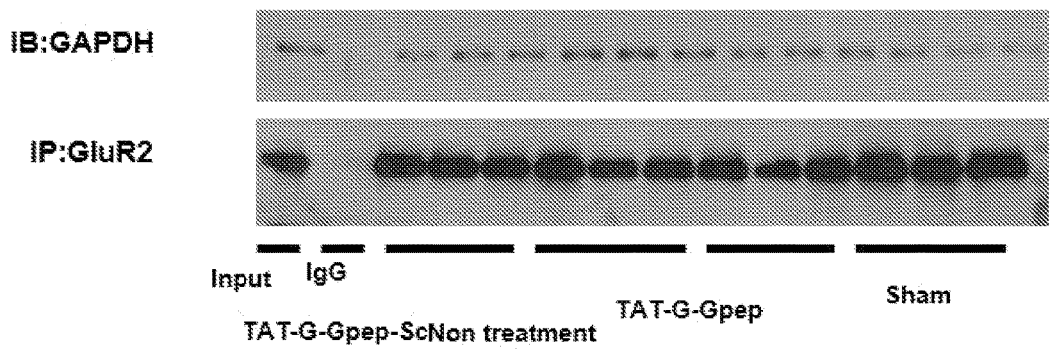
FIG. 2, Panels A-F, shows the characterization of the GluR2-GAPDH interaction in EAE animals. Panels A and B show coimmunoprecipitation of GAPDH with GluR2 from rat spinal cord tissues with a GluR2 antibody. $P<0.05$, n=4 compared to control. Panel C shows direct immunoprecipitation of GluR2 by GluR2 antibodies. Data are means±SEM and are analyzed by t-test. Panels D and F show densitometric analysis of coimmunoprecipitation of GAPDH with GluR2 from mice spinal cord tissues with a GluR2 antibody in different treatment groups. Panel C shows representative co-immunoprecipitation results of the interaction between GAPDH and GluR2 in the spinal cord of EAE modeling rats in different treatment groups. Blots and densitometry were done in triplicate. Data represents means±s.e.m. Differences between groups were accessed by Student Newman-Keuls post-hoc ANOVA.
Figure 2F:
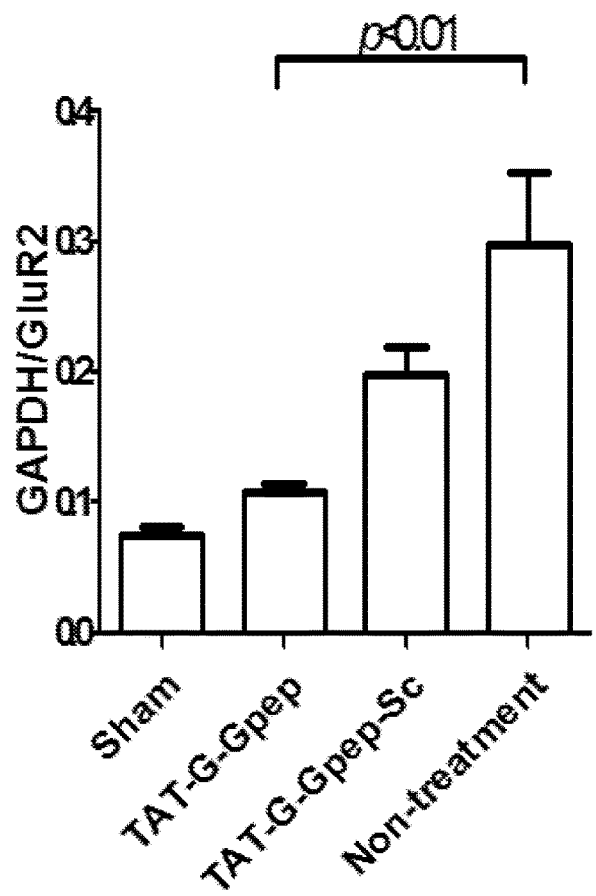

The present invention relates to polypeptides. The present invention also relates to polypeptides, compositions and methods for treatment and prophylaxis of MS.

The following description is of a preferred embodiment by way of example only and without limitation to the combination of features necessary for carrying the invention into effect.

In MS, an accumulation of glutamate is believed to be induced by activated immune cells, resulting in excessive stimulation of AMPAR, and eventually leading to loss of myelin, oligodendrocytes and some axons. Activation of AMPAR has been shown to cause the interaction between the GluR2 subunit of AMPAR and GAPDH (glyceraldehyde-3-phosphate dehydrogenase), a multifunctional protein that has a role in apoptosis. The polypeptide described herein has been previously shown to disrupt the GluR2-GAPDH interaction, and in rat models of global and focal ischemia, protects hippocampal neurons (PCT/CA2007/001539, the contents of which are incorporated herein by reference). As described herein, the G-Gpep polypeptide (also referred to as GluR2 NT1-3-2, Y142-K172 or SEQ ID NO:1 herein) improves neurological function in EAE rat and mouse treated with G-Gpep fused to the cell-membrane transduction domain of HIV-1 virus TAT, referred to herein as TAT-G-Gpep. Moreover, administration of TAT-G-Gpep to EAE rats/mice mitigates neuronal death, rescues demyelination, increases oligodendrocyte survival and reduces damage in the spinal cord. A fragment of this polypeptide has also been shown to immunoprecipitate GAPDH from hippocampal tissue homogenate, similar to TAT-G-Gpep suggesting that this polypeptide fragment (SEQ ID NO:5) also may be capable of similar effects.

According to an aspect of the present invention there is provided a polypeptide comprising or consisting of SEQ ID NO:5, or a fragment of SEQ ID NO:1 that comprises 20, 21, 22, 23, 24, 25, 26, 27, 28, 29, or 30 consecutive amino acids of SEQ ID NO:1, but preferably not all of SEQ ID NO: 1.

According to a further aspect, there is provided a polypeptide that is at least 80 identical in sequence to any one of the above, for example, 81%, 82%, 83%, 84%, 85%, 86%, 87%, 88%, 89%, 90%, 91%, 92%, 93%, 94%, 95%, 96%, 97%, 98% or 99%.

According to a further aspect of the invention, administering a polypeptide as described above or herein, or a composition comprising the polypeptide as described above or herein, for example, but not to be considered limiting in any manner, a polypeptide comprising SEQ ID NO: 5 or a polypeptide of between 31 and 200 amino acids comprising a GluR2 NT1-3-2 (Y142-K172) amino acid sequence defined by SEQ ID NO:1 or fragment thereof to a subject can be used for the treatment or prophylaxis of multiple sclerosis.

As shown in FIG. 1, the polypeptides preferably used in the present method include: GluR2 NT1-3-2 (Y142-K172) represented by amino acid sequence (SEQ ID NO:1) or a fragment thereof, for example, a polypeptide comprising SEQ ID NO:5 as described herein, or a sequence which is at least 80% identical to SEQ ID NO:1, or a fragment thereof such as SEQ ID NO:5 that binds to GAPDH and wherein said polypeptide does not encompass a naturally occurring full length GluR2 subunit polypeptide.

As provided above, variations of the polypeptide sequence of SEQ ID NO:1 are contemplated herein. For example, with respect to SEQ ID NO:1 (GluR2 NT1-3-2), but not to be considered limiting in any manner, one or more residues at positions 3, 5, 18, 21, 22, 23, 26 or 30 of SEQ ID NO:1 may be replaced by an alternate amino acid residue. For instance, but without wishing to be limiting, glutamine at position 3 may be replaced by another amino acid, for example, but not limited to lysine. Aspartic acid at position 5 may be replaced by another amino acid, for example, but not limited to threonine or glutamic acid. Serine at position 18 may be replaced by another amino acid, for example, but not limited to threonine. Glutamine at position 21 may be replaced by another amino acid, for example, but not limited to arginine. Alanine at position 22 may be replaced by another amino acid, for example, but not limited to valine or isoleucine. Valine at position 23 may be replaced by another amino acid, for example, but not limited to isoleucine. Serine at position 26 may be replaced by another amino acid, for example, but not limited to threonine. Lysine at position 30 may be replaced by another amino acid, for example, but not limited to arginine. These modifications have not been tested but are thought to provide the desired effect(s) as described herein. Other modifications are also possible and are contemplated herein. Further, the present invention contemplates variations wherein one or more of the replacements noted above are present in the polypeptide.

Naturally occurring full length GluR2 polypeptides and the sequences thereof are known in the art. For example, a search of the National Center for Biotechnology Information using sequence information provided herein can be used to identify naturally occurring full length GluR2 protein sequences.

The present invention also provides for fragments of the GluR2 NT1-3-2 (Y142-K172) amino acid sequence (SEQ ID NO:1), that do not encompass a naturally occurring full length GluR2 subunit, but rather is between about 20 and 200 amino acids in length, for example, but not limited to 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 170, 180, 190, 200 or any number of amino acids therein between. The present invention also encompasses polypeptides comprising the GluR2 NT1-3-2 (Y142-K172) amino acid sequence (SEQ ID NO:1) or a fragment thereof such as SEQ ID NO:5 that may be defined by a range of lengths of any two of the values provided above, or any values therein between. For example, but not to be limiting in any manner, the present invention provides a polypeptide comprising the GluR2 NT1-3-2 (Y142-K172) amino acid sequence (SEQ ID NO:1) or SEQ ID NO:5 that is between 20 and 100, 20-200, 20-250, 25-200, 25-250, 27-300 amino acids in length, and the like.

The present invention also contemplates polypeptides having an amino acid sequence that comprises between about 80% to 100% sequence identity, for example, but not limited to 80%, 81%, 82%, 83%, 84%, 85%, 86%, 87%, 88%, 89%, 90%, 91%, 92%, 93%, 94%, 95%, 96%, 97%, 98%, 99% or 100% identity to the amino acid sequences described above. Further, the polypeptides may be defined as comprising a range of sequence identities defined by any two of the values listed above.

The present invention also contemplates polypeptides that comprise fragments of GluR2 NT1-3-2 (Y142-K172) amino acid sequence (SEQ ID NO:1), for example 30, 29, 28, 27, 26, 25, 24, 23, 22, 21, and 20 amino acids. Further, the present invention also contemplates fragments that exhibit at least about 80% identity, preferably 85%, 90%, 95%, 96%, 97%, 98%, 99% or 100% identity to the polypeptides described above. The present invention also contemplates polypeptides that comprise fragments of GAPDH(2-2-1-1), for example 29, 28, 27, 26, 25, 24, 23, 22, 21, 20, 19, 18, 17, 16, 15, 14, 13, 12, 11, 10, 9, 8, and 7 amino acids. The fragments may comprise N-terminal deletions, C-terminal deletions, internal deletions or any combination thereof.

It is also contemplated that the GluR2 NT1-3-2 (Y142-K172) amino acid sequence (SEQ ID NO:1) or SEQ ID NO:5 may comprise part of a fusion protein, for example, but not limited to a polypeptide that further comprises a heterologous polypeptide or protein, for example, a carrier protein, a protein transduction domain or the like. For example, but not wishing to be limiting in any manner, the polypeptide of the present invention may be fused to a protein transduction domain to facilitate transit across lipid bilayers or membranes, for example, but not limited to as described in U.S. Publication 2002/0142299, U.S. Pat. No. 5,804,604, U.S. Pat. No. 5,747,641, U.S. Pat. No. 5,674,980, U.S. Pat. No. 5,670,617, and U.S. Pat. No. 5,652,122; PCT publication WO01/15511, US Publication 2004/0209797, PCT Publication WO99/07728, US Publication 2003/0186890, all of which are herein incorporated by reference.

It is also contemplated that the polypeptide of the present invention may be attached either covalently or non-covalently to a non-protein substrate or molecule, for example, but not limited to polyethylene glycol (PEG), dextran or polydextran bead or the like, a support such as, but not limited to a multi-well plate, coverslip, array, micro-chip or the like. It is also contemplated that the polypeptide, non-protein substrate, molecule or any combination thereof may be labeled, for example with a purification tag, a radioactive or fluorescent group, enzyme or the like.

The present invention also provides nucleic acids encoding the polypeptides as described above. In an embodiment of the present invention which is not meant to be limiting, there is provided a nucleic acid encoding a polypeptide comprising the GluR2 NT1-3-2 (Y142-K172) amino acid sequence (SEQ ID NO:1) or SEQ ID NO:5 that does not encode a naturally occurring full length GluR2 subunit. More preferably, but not wishing to be limiting in any manner, the present invention provides a nucleic acid encoding a polypeptide of between 20 and 200 amino acids and comprises the GluR2 NT1-3-2 (Y142-K172) amino acid sequence (SEQ ID NO:1) or SEQ ID NO:5. An exemplary nucleic acid sequence, not meant to be limiting in any manner is shown FIG. 1B as represented by SEQ ID NO:2.

The present invention also contemplates compositions comprising one or more of the polypeptides and/or nucleic acids of the present invention. The compositions may comprise one or more diluents, delivery vehicles, excipients, for example, but not limited to pharmaceutically acceptable excipients as would be known in the art, buffers, media, solvents, solutions, carriers or the like. Such components alone or in any combination may provide a dosage form for using or administering the polypeptides or nucleic acids of the present invention to a solution, cell, cell culture, tissue, organ or subject, for example, but not limited to a human subject.

To determine whether a nucleic acid exhibits identity with the sequences presented herein, oligonucleotide alignment algorithms may be used, for example, but not limited to a BLAST (GenBank, using default parameters: Program: blastn; Database: nr; Expect 10; filter: default; Alignment: pairwise; Query genetic Codes: Standard(1)), BLAST2 (EMBL using default parameters: Matrix BLOSUM62; Filter: default, echofilter: on, Expect:10, cutoff: default; Strand: both; Descriptions: 50, Alignments: 50), or FASTA, search, using default parameters. Polypeptide alignment algorithms are also available, for example, without limitation, BLAST 2 Sequences (using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH.

A polypeptide of the invention can be synthesized in vitro or delivered to a cell in vivo by any conventional method. As a representative example of an in vitro method, the polypeptide may be chemically synthesized in vitro, or may be enzymatically synthesized in vitro in a suitable biological expression system. As a representative example of an in vivo method, a DNA, RNA, or DNA/RNA hybrid molecule comprising a nucleotide sequence encoding a polypeptide of the invention is introduced into an animal, and the nucleotide sequence is expressed within a cell of an animal.

The nucleotide sequence may be operably linked to regulatory elements in order to achieve preferential expression at desired times or in desired cell or tissue types. Furthermore, as will be known to one of skill in the art, other nucleotide sequences including, without limitation, 5' untranslated region, 3' untranslated regions, cap structure, poly A tail, translational initiators, sequences encoding signalling or targeting peptides, translational enhancers, transcriptional enhancers, translational terminators, transcriptional terminators, transcriptional promoters, may be operably linked with the nucleotide sequence encoding a polypeptide (see as a representative example "Genes VII", Lewin, B. Oxford University Press (2000) or "Molecular Cloning: A Laboratory Manual", Sambrook et al., Cold Spring Harbor Laboratory, 3rd edition (2001)). A nucleotide sequence encoding a polypeptide or a fusion polypeptide comprising the polypeptide may be incorporated into a suitable vector. Vectors may be commercialy obtained from companies such as Stratagene or InVitrogen. Vectors can also be individually constructed or modified using standard molecular biology techniques, as outlined, for example, in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, but are not limited to, transcriptional promoters, transcriptional enhancers, transcriptional terminators, translational initiators, translational terminators, ribosome binding sites, 5' untranslated region, 3' untranslated regions, cap structure, poly A tail, origin of replication, detectable markers, afffinity tags, signal or target peptide, Persons skilled in the art will recognize that the selection and/or construction of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

As described herein, and unless clearly indicated otherwise, the term "mini-gene" means the expression product of a nucleic acid or nucleotide sequence encoding and capable of expressing a polypeptide in a cell. For example, but not wishing to be considered limiting in any manner, a mini-gene includes a nucleic acid or nucleotide sequence encoding and capable of expressing the polypeptide, for example, the polypeptide comprising the GluR2 NT1-3-2 (Y142-K172) amino acid sequence (SEQ ID NO:1) or SEQ ID NO:5 in a cell.

The DNA, RNA, or DNA/RNA hybrid molecule may be introduced intracellularly, extracellularly into a cavity, interstitial space, into the circulation of an organism, orally, or by any other standard route of introduction for therapeutic molecules and/or pharmaceutical compositions. Standard physical methods of introducing nucleic acids include, but are not limited to, injection of a solution comprising RNA, DNA, or RNA/DNA hybrids, bombardment by particles covered by the nucleic acid, bathing a cell or organism in a solution of the nucleic acid, or electroporation of cell membranes in the presence of the nucleic acid.

A nucleic acid may be introduced into suitable eukaryotic cells ex vivo and the cells harbouring the nucleic acid can then be inserted into a desired location in an animal. A nucleic acid can also be used to transform prokaryotic cells, and the transformed prokaryotic cells can be introduced into an animal, for example, through an oral route. Those skilled in the art will recognize that a nucleic acid may be constructed in such a fashion that the transformed prokaryotic cells can express and secrete a polypeptide of the invention. Further, a nucleic acid may also be inserted into a viral vector and packaged into viral particles for efficient delivery and expression.

The polypeptides of the present invention or the nucleic acids encoding the polypeptides of the present invention may be formulated into any convenient dosage form as would be known in the art. The dosage form may comprise, but is not limited to an oral dosage form wherein the agent is dissolved, suspended or the like in a suitable excipient such as but not limited to water or saline. In addition, the agent may be formulated into a dosage form that could be applied topically or could be administered by inhaler, or by injection either subcutaneously, into organs, or into circulation. An injectable dosage form may include other carriers that may function to enhance the activity of the agent. Any suitable carrier known in the art may be used. Also, the agent may be formulated for use in the production of a medicament. Many methods for the productions of dosage forms, medicaments, or pharmaceutical compositions are well known in the art and can be readily applied to the present invention by persons skilled in the art.

According to the present invention there is also provided a method of inhibiting GluR2 subunit association with GAPDH comprising: administering a polypeptide as described herein, for example a polypeptide comprising the GluR2 NT1-3-2 (Y142-K172) amino acid sequence (SEQ ID NO:1) or SEQ ID NO:5 to a solution, cell, cell culture, tissue or subject comprising GluR2 subunit and GAPDH. The method may be practiced in vitro or in vivo. In an embodiment wherein the method is practiced in vivo, the method may be practiced in a human subject. The human subject may have or be susceptible to multiple sclerosis.

In still a further embodiment of the present invention, which is not meant to be limiting in any manner, there is provided a method for treatment or prophylaxis of multiple sclerosis comprising, administering: a polypeptide as described herein, for example, a polypeptide comprising the GluR2 NT1-3-2 (Y142-K172) amino acid sequence (SEQ ID NO:1) or SEQ ID NO:5; or a nucleic acid capable of expressing a polypeptide comprising the GluR2 NT1-3-2 (Y142-K172) amino acid sequence (SEQ ID NO:1) or SEQ ID NO:5 to a subject in need thereof. As will be evident to a person of skill in the art, an embodiment that comprises administering a nucleic acid as described above, further comprises the step of expressing nucleic acid in the subject.

It follows from the description above that the present invention also contemplates a polypeptide as described herein for use in the prophylaxis and/or treatment of neurological conditions such as MS in a subject. Other uses as described herein are also contemplated as are uses for the treatment of or for the production of a medicament for the prophylaxis and/or treatment of neurological conditions such as MS in a subject.

The present invention also contemplates a method as defined above wherein the polypeptide is administered prior to, during, after or both prior to and after an event that is associated with multiple sclerosis, for example, but not limited to weakness, fatigue, loss of vision, cognitive impairment and impaired balance and coordination. For example, but not to be considered limiting in any manner, subjects diagnosed with MS may be administered the polypeptide of the present invention at one or more intervals after being diagnosed with the condition, preferably prior to, during or after an MS episode. In another embodiment, the polypeptide is administered as prophylactic treatment to individuals being genetically predisposed to the development of MS or have had one or more MS episodes in the past and are at risk to having another episode.

EXAMPLES

General Methodology

Animals Model and Tissue Harvest

C57/B16 mice (4-6 weeks old) used in this study were all purchased from Charles Rivers. All animal studies were approved by the Canada Animal Care Committee. Briefly, EAE was induced in C57/B16 mice by subcutaneous (s.c.) immunization with 200 μg of the murine myelin oligodendrocyte glycoprotein (MOG) peptide 35-55 (MEVGWYR-SPFSRVVHLYRNGK) SEQ ID NO:6 emulsified in 100 μl of complete Freund's Adjuvant. Two hundreds ng of pertussis toxin in 100 μl of phosphate-buffered saline (PBS) were injected i.p. on the day of immunization (day 0) and two days later. 1 mM GluR2nt1-3-2 peptide was injected intreperitonally (i.p.) daily starting on day 10 after immunization. Control mice received GluR2NT1-3-2-SCRM (scrambled GluR2NT1-3-2 polypeptide) in the same concentration.

The clinical score was assessed daily from day 1 after the immunization. a 0-4 scoring system was used: 0, no obvious signs; 0.5, Distal paresis of the tail; 1, Complete tail paralysis; 1.5, Paresis of the tail and mild hind leg paresis; 2, unilateral severe hind leg paresis; 2.5, bilateral severe hind limb paresis; 3, complete bilateral hind limb paralysis; 3.5, complete bilateral hind limb paralysis and paresis of one front limb; 4, complete paralysis (tetraplegia), moribund state, or death.

At day 30, mice were sacrificed by overdose anesthesia, and the spinal cord was dissected for co-immunoprecipitation analysis. For analysis of central nervous system infiltrates, brain and spinal cord tissues were collected and mononuclear cells were prepared by Percoll gradient centrifugation. For immunological analysis, splenocytes cells were dissected and cultured in vitro. For histological analysis, the same tissue samples were immediately fixed in 4% (wt/vol) paraformaldehyde. Frozen sections of spinal cord were stained with Luxol fast blue for analysis of inflammation and demyelination, respectively.

Lymphocytes Proliferation Assay

Lymphocytes of the EAE mice in different treatment groups were obtained from mice spleen. Briefly, mice were sacrificed and spleen were dissected. Spleen tissues were placed in DMEM medium and cut into small pieces (1 mm$^3$), and then passed through a 40 μm cell strainer in DMEM medium. Red blood cell lysis buffer was used to remove all the red blood cells. After centrifugation, single cell suspensions were cultured in 96 well plates and stimulated with MOG 35-55 peptide in different concentrations (0 μM, 10 μM, 100 μM) or PHA (5 μM) for 72 h. A 10 mL aliquot containing 1 mCi 3H-thymidine was added prior to the final 18 h of culture. Cells described above were harvested onto glass-fiber filters for the assay of radioactivity by a liquid β-scintillation counter (Perkin-Elmer, Wellesley, Mass., USA).

Bioplex Protein Array

Cytokine measurement was performed by Bioplex Protein Array (Bio-Plex Pro™ Mouse Cytokine 23-plex Assay) from Bio-Rad as per manufacturer's instruction. EAE mice serum, culture supernatant of spleenocytes in different treatment groups and supernatant of brain infiltrated leukocyte culture were used for bioplex protein array in duplicates. The standard curves were optimized automatically by the software (Bioplex manager) and verified manually. The Bioplex manager software was used to calculate cytokine concentrations. Data is expressed as Mean±SEM.

Immunofluoresence

Frozen coronal sections of EAE mice spinal cord (10 µm) thickness were cut using a microtome cryostat system (Bright Instruments 5030). All sections were initially incubated in blocking solution (0.1 m PBS, 1% Triton X-100, 0.5% Tween 20, 2% skim milk) or serum-free protein block (Dako Cytomation) for 1 h at room temperature to reduce nonspecific background and then incubated with primary and secondary antibodies overnight at 4° C. The following primary antibodies were used: anti-Iba1 (1:200; Dako), anti-Neurofilament H (1:200), anti-CC1, anti-CNPase (1:200), and anti-NeuN (1:200). Fluorescent secondary antibodies conjugated to Alexa 488 or Rhodamine Red-X (1:200; Invitrogen) or Cy3 (1:100; Jackson ImmunoResearch Laboratories) were used for detection of primary antibodies.

Flow Cytometry

Flow cytometry was conducted using spleenocytes obtained from different groups. Briefly, cells were incubated with anti-CD4(FITC BD), and anti-CD8(Cy7, BD) or anti-CD11b(PE, BD) and anti-CD11c (Cy7, BD) for 1 h at room temperature. After washing, cells was fixed with fixation buffer (BD) for 30 min and filtered using 80 µm cell strainer. Samples were analyzed within 24 h with BD FACScan (BD Biosciences) using Cell Quest software (BD Biosciences). Isotypematched, PE- and FITC-conjugated mAb of irrelevant specificity were tested as negative controls.

Example 1

GluR2-GAPDH Interaction is Increased in the Spinal Cord of EAE Rats and Mice

To investigate whether the GluR2-GAPDH interaction plays a role in the pathology of MS, GluR2-GAPDH complex formation was tested to determine if the formation is altered in the spinal cord of EAE rats. EAE was induced by immunizing Lewis rats with guinea pig myelin basic protein emulsified in Freund's complete adjuvant containing *Mycobacterium tuberculosis*. Neurological decline was observed beginning 9-11 days after immunization, consistent with previous reports (Schluesener, H. J., et al., *J Neuroimmunol* 18, 341-351, 1988). Rats were sacrificed on day 14 (previous studies indicate that the neurological decline reaches a peak on day 13 after immunization), and spinal cord protein was extracted to examine the interaction between GluR2 and GAPDH by co-immunoprecipitation. Consistent with the results from rat ischemia models, GluR2-GAPDH interaction was increased in EAE rat spinal cord protein extract in comparison to control rats, by using GluR2 antibody to co-immunoprecipitate GAPDH (FIG. 2A, 2B) (n=4, $p<0.05$; Data are means±SEM. and are analyzed by t-test). There was no difference in directly-immunoprecipitated GluR2 levels between EAE and control rats (FIG. 2C). Similar results were also obtained in EAE mice (FIG. 2D,F). Mouse EAE was induced using $MOG_{35-55}$ emulsified with CFA. These mice started to develop MS-like symptoms on day 10. At day 13, treatment of mice daily was started with either TAT-G-Gpep or TAT-G-Gpep-Sc (I.P.). Mice were sacrificed on day 28 for extraction of spinal cord protein. The interaction between GluR2 and GAPDH was examined by co-immunoprecipitation, and an enhanced GluR2-GAPDH interaction was found in EAE mice. Injection of TAT-G-Gpep was able to disrupt the GluR2-GAPDH interactions.

Example 2

Figure 3:
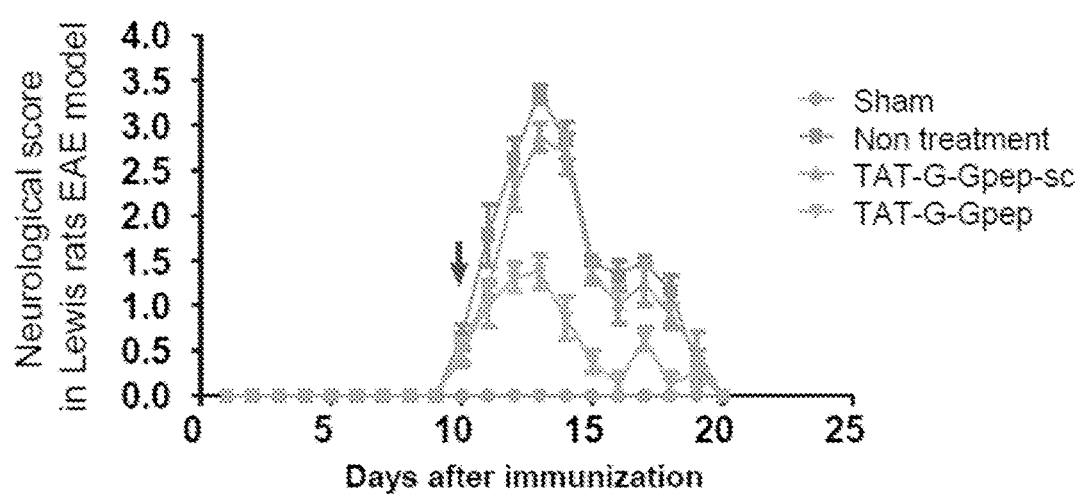
FIG. 3 represents a neurological assessment of EAE rats and the effect of treatment with TAT-G-Gpep. Treatments were started daily on day 10 after immunization. Rats were treated with TAT-G-Gpep, TAT-G-Gpep-sc until day 20.
Figure 4:
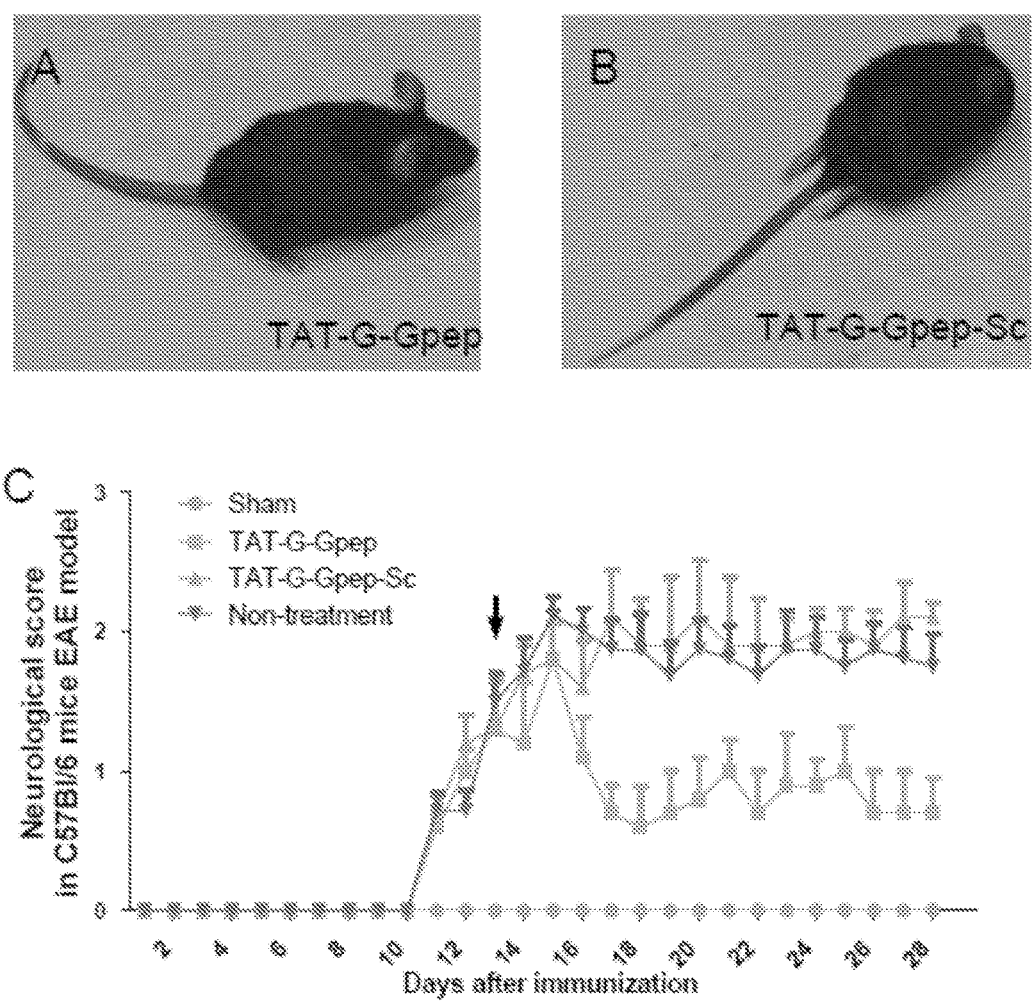
FIG. 4, Panels A-C, provides results of EAE modeled mice treated with TAT-G-Gpep (Panel A) and TAT-G-Gpep-Sc (Panel B). Panel C, Clinical EAE scores (means±s.e.m) over time of four groups vaccinated with MOG35-55 on day 0 and treated intraperitoneally daily with TAT-G-Gpep and Scramble TAT G-Gpep from day 13 (arrow). Starting from Day 13, ($P<0.05$). Data was analyzed by two-way ANOVA.

Disruption of GluR2-GAPDH Interaction Improved Neurological Function in EAE Rats and Mice An interfering peptide (G-Gpep) also known as GluR2 NT1-3-2 having the amino acid sequence YYQWDKFAYLYDSDRGLSTLQAVLDSAAEKK (SEQ ID NO:1) capable of disrupting GluR2-GAPDH interactions and protecting neurons from ischemia-induced cell death in animal models of ischemic stroke was used. A scrambled G-Gpep peptide (G-Gpep-sc or G-Gpep-scrambled) having the amino acid sequence YGRKKRRQRRRAFDLSQYDLKWQVDYLKYDYGTASELRASA (SEQ ID NO:4) was used as a control peptide. To enable all peptides to permeate the cell membrane, they are fused to the cell-membrane transduction domain of the HIV-type 1 virus: TAT domain. Intraperitoneal (IP) injection of TAT-G-Gpep was chosen in the current experiment due to the requirement for repeated injections in the EAE models. The daily peptide injection regimen was started on the tenth day after rats are immunized and the $13^{th}$ day after mice are immunized, based on the previous studies on AMPAR antagonists in the treatment of MS (Pitt, D., et al., *Nat Med* 6, 67-70, 2000; Smith, T., et al., *Nat Med* 6, 62-66, 2000; Kanwar, J. R., et al., *Brain* 127, 1313-1331, 2004). The neurological score was rated each day, one hour after peptide injection. As shown in FIG. 3 (rats) and 4 (mice), IP application of TAT-G-Gpep (3 nmol/g) daily to the immunized animals significantly reduced the cumulative neurological score compared to EAE rat/mice without peptide or TAT-G-Gpep-sc treated EAE rats/mice.

Example 3

Disruption of GluR2-GAPDH Interaction Mitigated AMPAR Toxicity-Associated Injury in the Spinal Cord of EAE Rats/Mice Loss of myelin, oligodendrocytes and some axons are core features of MS pathology. As such, spinal cord sections from the lumbar region of EAE rats and mice treated with TAT-G-Gpep peptide were examined in comparison to TAT-G-Gpep-sc as a control.

Figure 5:
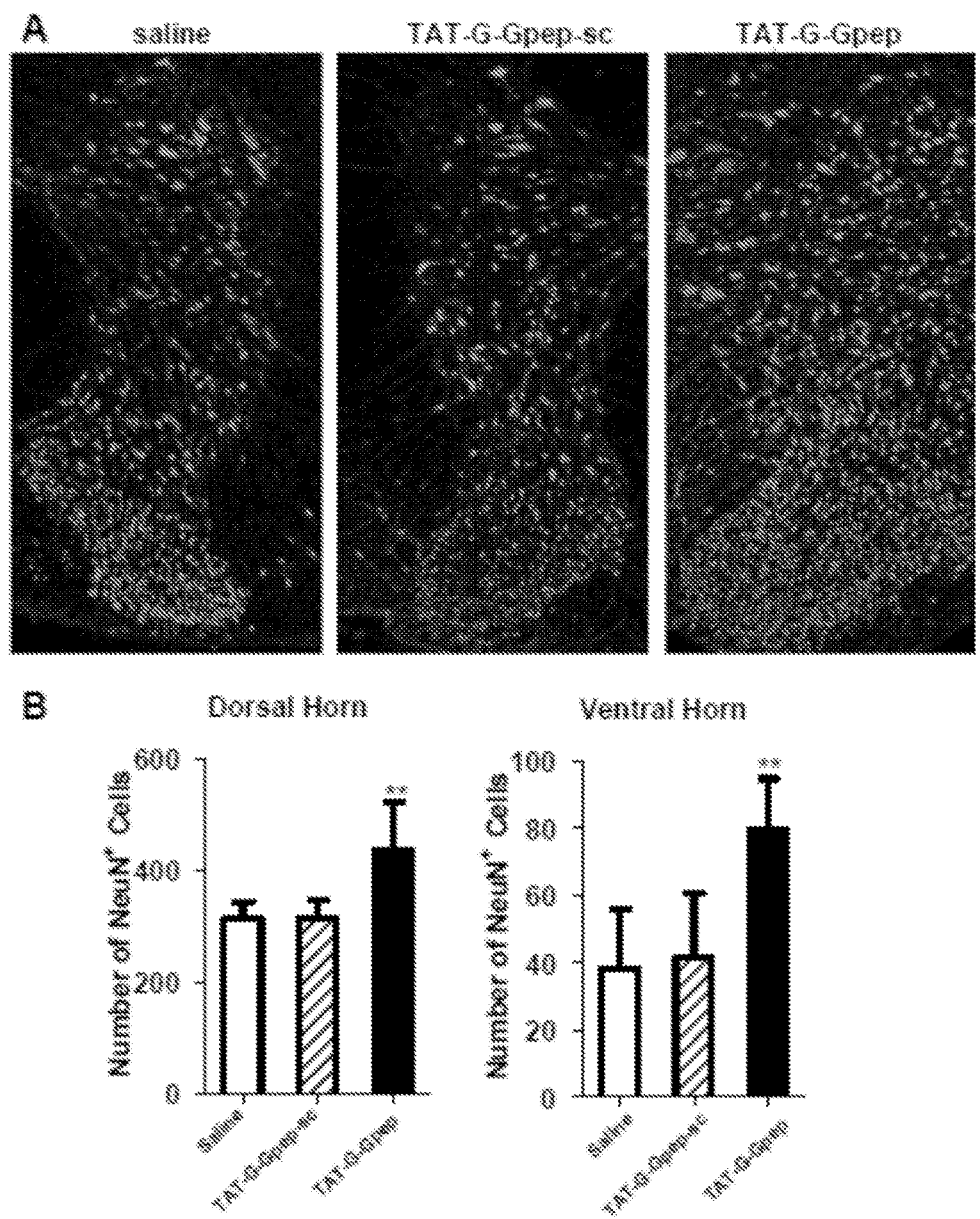
FIG. 5, Panels A-B, shows rescue of neuronal number in lumber spinal cord with TAT-G-Gpep peptide treatment. Panel A represents Neu-N-immunostained fluroscence sections in saline, TAT-G-Gpep-sc treated and TAT-G-Gpep treated EAE rats shown at 5× magnification. Panel B shows the quantification of NeuN+ cells in both dorsal and ventral horns revealed a significant increase in TAT-G-Gpep peptide-treated EAE rats (n=6-9) as compared to TAT-G-Gpep-sc treated EAE rats. Data are presented as means±s.e.m. **$p<0.01$ vs saline.
Figure 6:
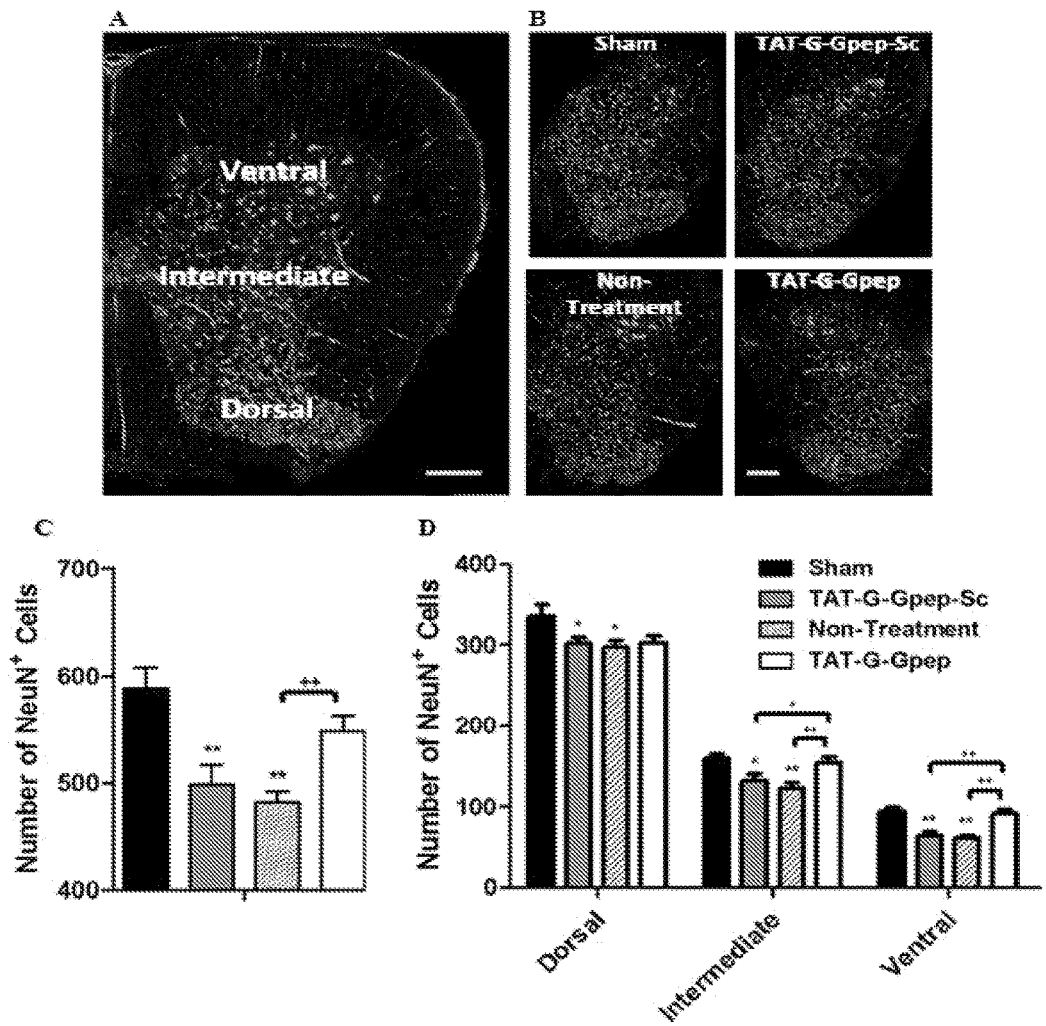
FIG. 6, Panels A-D, shows neuronal rescue with TAT-G-Gpep treatment in EAE mouse lumbar spinal cord. Panel A, NeuN-immunostained image of lumbar spinal cord delineated into ventral, intermediate and dorsal zones. Scale Bar, 100 µm. Panel B, Representative images of NeuN+ cells in sham, TAT-G-Gpep-Sc, non-treated and TAT-G-Gpep-treated mouse spinal cords. Scale Bar, 100 µm. Quantification of Panel C, total neurons and Panel D, in dorsal, intermediate and ventral zones with different treatments. There were significantly fewer total neurons in both non-treated and peptide-treated mice spinal cords when compared to sham animals. Peptide-treatment resulted in a significantly more neuronal numbers in the intermediate and ventral zones vs. non-treated and TAT-G-Gpep-Sc-treated mice. All data are shown as mean±SEM; *$p<0.05$, **$p<0.01$ vs sham; ++$p<0.01$.

IP injection of TAT-G-Gpep was found to enhance spinal cord neuron density as indexed by counting NeuN+ cells in dorsal and ventral horns of the lumbar region of EAE rats (FIG. 5)/mice (FIG. 6) compared to EAE rats/mice treated with TAT-G-Gpep-sc.

Figure 7:
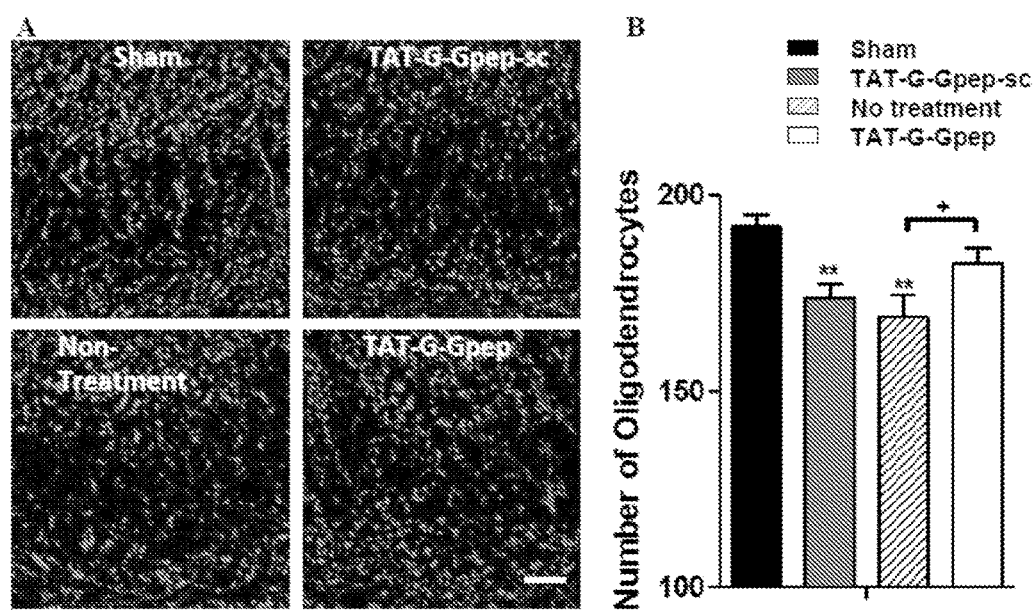
FIG. 7, Panels A-B, shows that TAT-G-Gpep treatment promotes oligodendrocytes survival in rat spinal cords with EAE. Panel A represents CNPase-immunolabelled oligodendrocytes in sham, saline, non-treated and TAT-G-Gpep treated rat spinal cords. Scale bar, 20 µm. Panel B represents quantification of the number of CNPase-reactive oligodendrocytes in dorsal regions of rat spinal cords. All data are represented as mean±s.e.m., **$p<0.01$ vs sham, +$p<0.05$.
Figure 8:
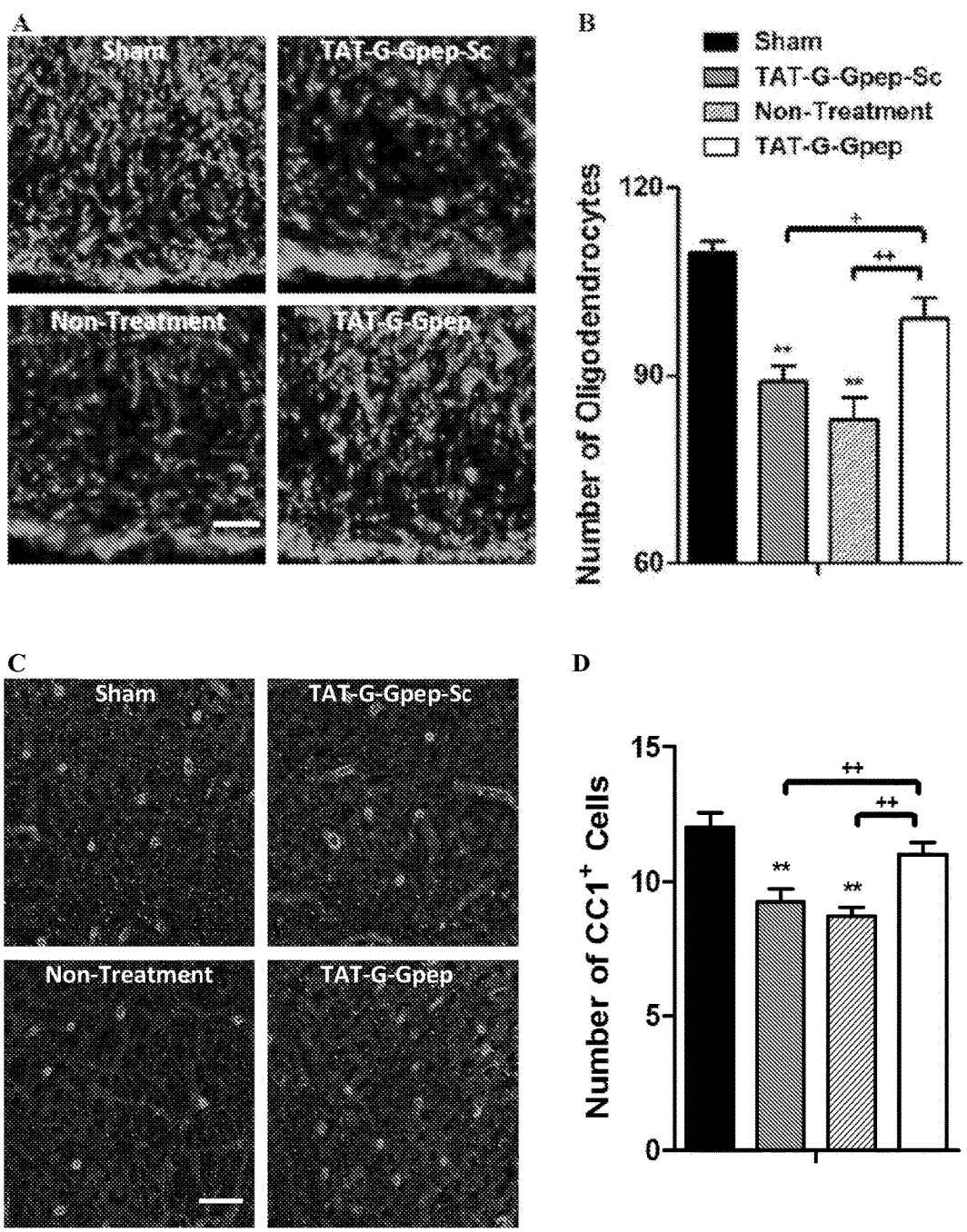
FIG. 8, Panels A-D, shows TAT-G-Gpep treatment promotes oligodendrocyte survival in mouse EAE spinal cord. Representative images of (Panel A) CNPase-reactive and (Panel C) CC1-immmunolabeled oligodendrocytes in sham, TAT-G-Gpep-Sc, non-treated and TAT-G-Gpep-treated mouse spinal cords. Scale Bar, 15 µm. Quantification of the number of (Panel B) CNPase- and (Panel D), CC1-labeled oligodendrocytes in dorsal regions of mouse spinal cord. Oligodendrocyte numbers were significantly lower in scrambled peptide and non-treated mice when compared to sham, while peptide treatment significantly rescued oligodendrocyte numbers. All data are shown as mean±SEM; **$p<0.01$ vs sham; ++$p<0.01$.

IP injection of TAT-G-Gpep was also found to promote oligodendrocyte survival as indexed by CNPase-immunolabeled oligodendrocytes in spinal cord of EAE rats (FIG. 7)/mice (FIG. 8) compared to EAE rats/mice treated with TAT-G-Gpep-sc.

Figure 9:
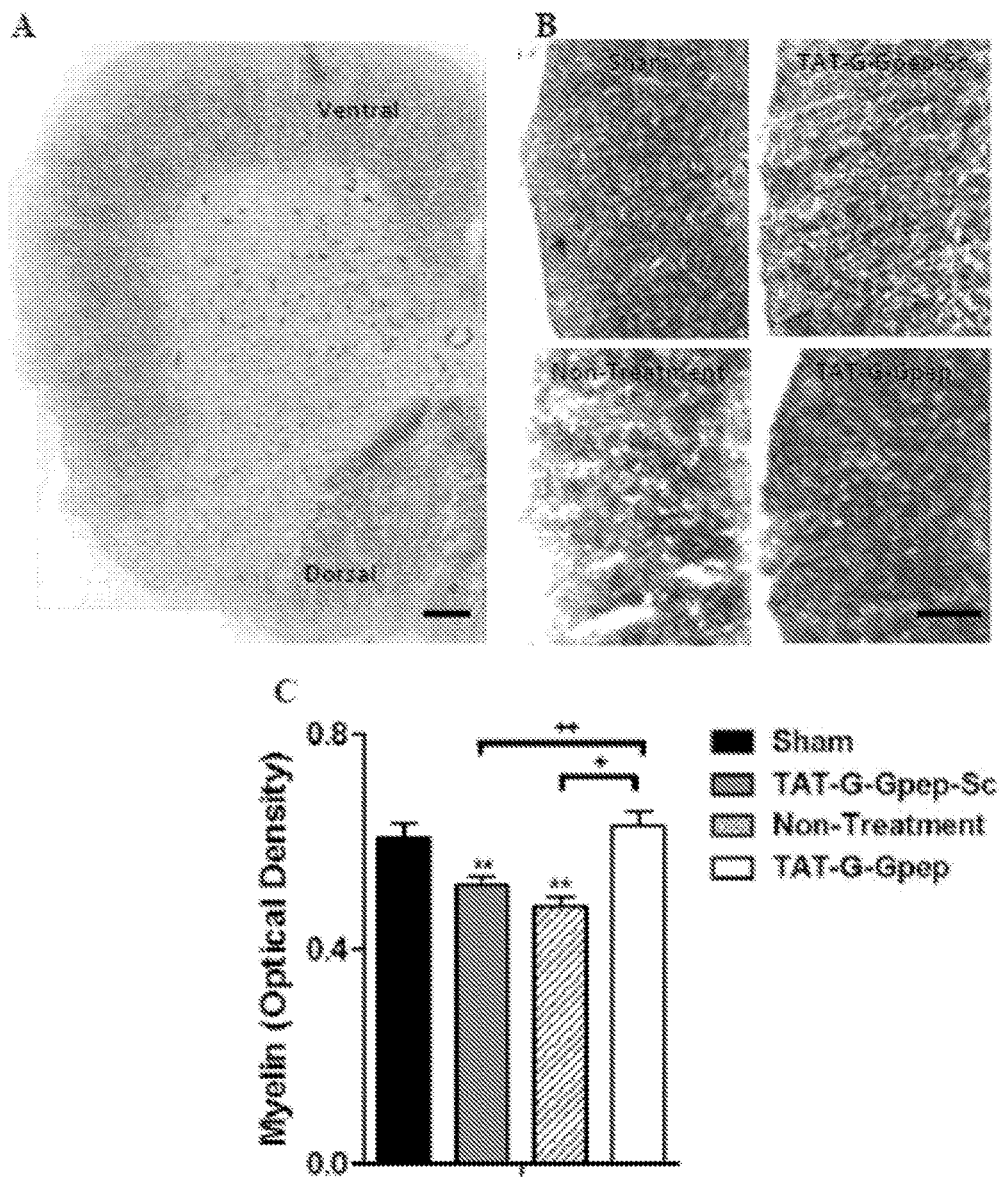
FIG. 9, Panels A-C, shows that TAT-G-Gpep treatment rescues demyelination in EAE rat spinal cords. Panel A shows Luxol Fast Blue staining of myelin (blue) in rat dorsal and ventral regions. Scale bar, 100 µm. Panel B represents quantification of myelin in both dorsal and ventral funiculus in rat spinal cords with different treatments. Panel C Images were converted to grey scale and calculated according to precalibrated values, and myelin density was measured in optical density. All data are represented as mean±s.e.m., **$p<0.01$ vs sham, +$p<0.05$, ++$p<0.01$.
Figure 10:
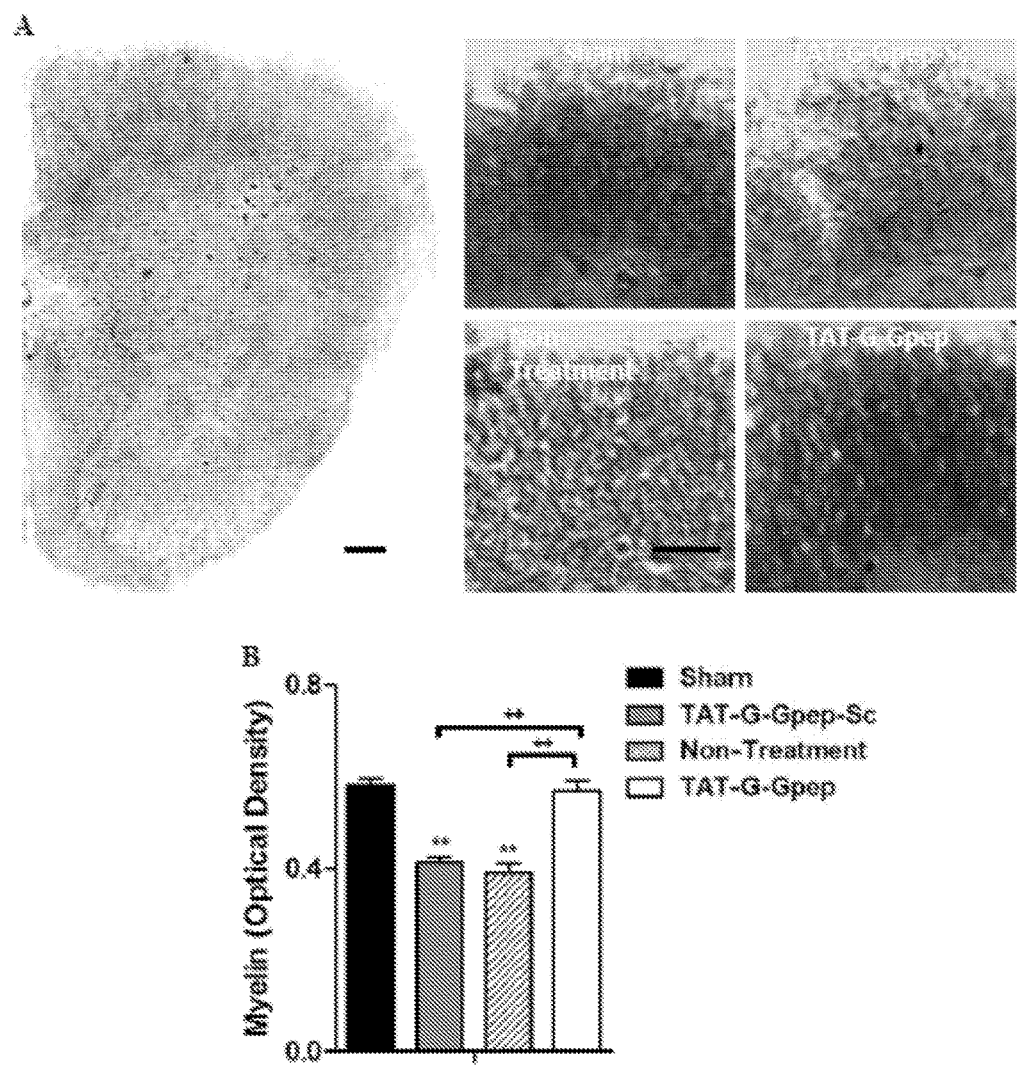
FIG. 10, Panels A-B, shows that TAT-G-Gpep treatment rescues demyelination in EAE mouse spinal cord. Panel A shows Luxol Fast Blue staining of myelin in mouse spinal cord and representative images of Luxol Fast Blue stains (gray scale) in sham, TAT-G-Gpep-Sc, non-treated and TAT-G-Gpep-treated mouse spinal cords. Scale bar, 50 µm. Panel B represents quantification of myelin in the ventral funiculus in mouse spinal cord with different treatments. Panel C Images were converted to grey scale and calculated according to precalibrated values, and myelin density was measured in optical density. Significant demylenation was observed in scrambled peptide and non-treated mice when compared to sham. TAT-G-Gpep treatment resulted in significant rescue of myelination vs both scrambled peptide or non-treated groups. All data are represented as mean±s.e.m., **$p<0.01$ vs sham, ++$p<0.01$.

Luxol Fast Blue staining of myelin indicated that IP injection of TAT-G-Gpep rescues demyelination in the spinal cord of EAE rats (FIG. 9)/mice (FIG. 10) compared to EAE rats/mice treated with TAT-G-Gpep-sc.

Figure 11:
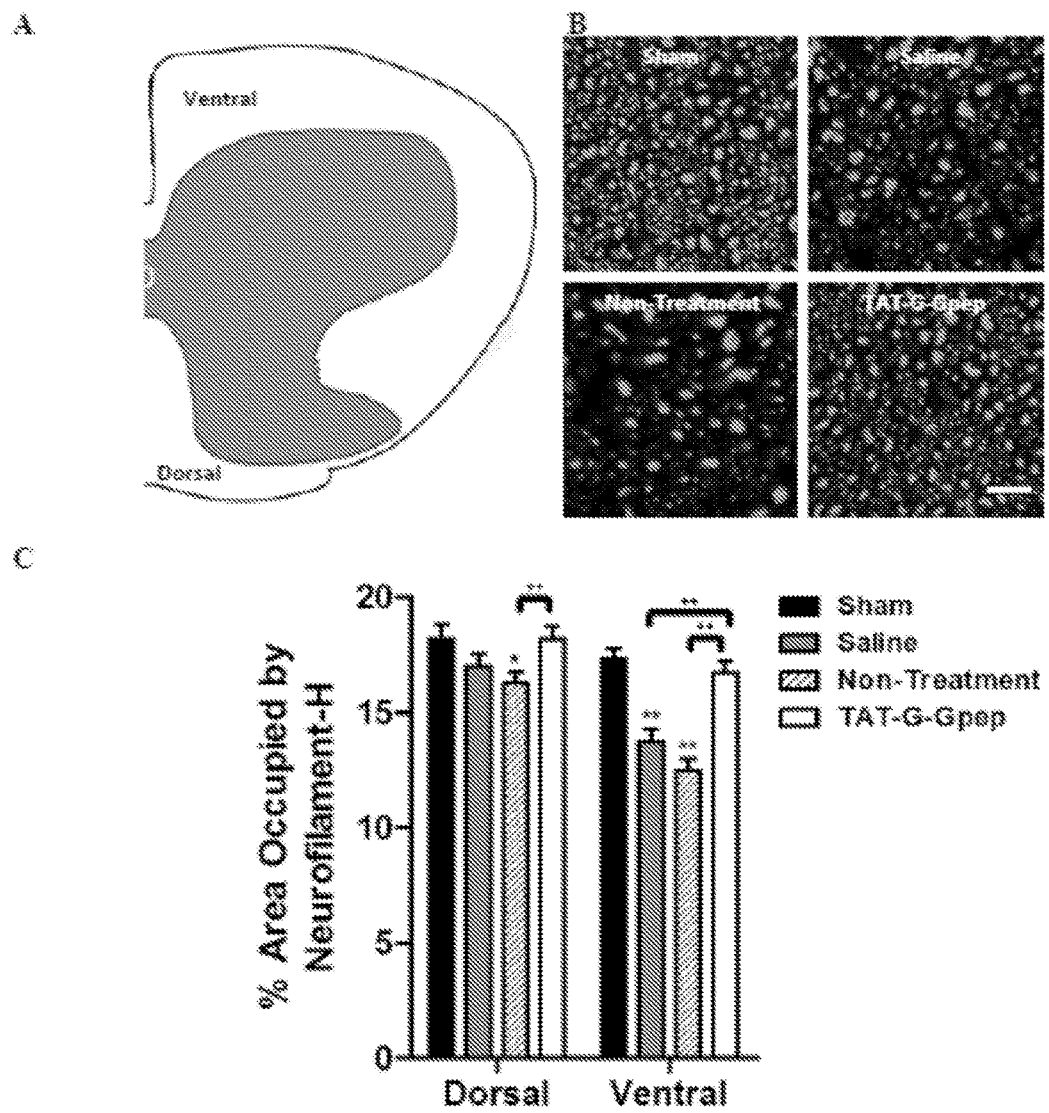
FIG. 11, Panels A-C, shows that TAT-G-Gpep treatment rescues axonal density in rat spinal cord with EAE. Panel A is a schematic diagram of coronal spinal cord section showing regions of interest in dorsal and ventral funiculus. Panel B are representative images of neurofilament-H immunostained in sham, saline, non-treated and TAT-G-Gpep-treated rat spinal cords. Scale bar, 20 µm. Panel C represents quantification of the percentage area occupied by neurofilament-H in dorsal and ventral regions of rat spinal cords. All data are represented as mean±s.e.m., **$p<0.01$ vs sham, ++$p<0.01$.
Figure 12:
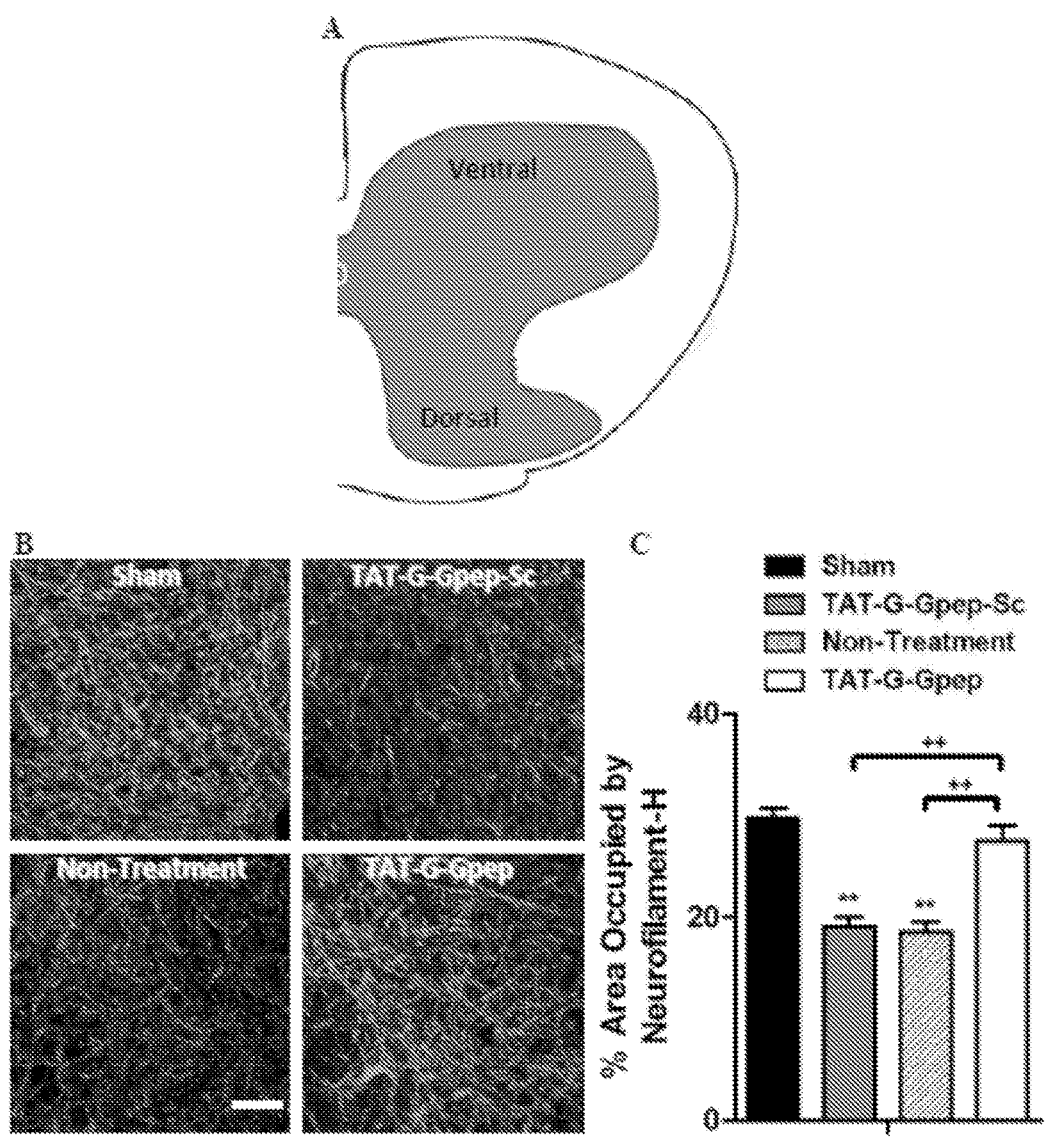
FIG. 12, Panels A-C, shows that TAT-G-Gpep treatment rescues axonal density in mice spinal cord with EAE. Panel A is a schematic diagram of coronal spinal cord section showing regions of interest in dorsal and ventral horns of the grey matter. Panel B are representative images of neurofilament-H immunostained in sham, saline, non-treated and TAT-G-Gpep-treated mouse spinal cords. Scale bar, 15 μm. Panel C represents quantification of the percentage area occupied by neurofilament-H in mouse spinal cords. The area occupied by neurofilament-H was significantly lower in scrambled peptide and non-treated mice when compared to sham, while peptide treated mice showed a significant rescue in axon density and was comparable to sham controls. All data are represented as mean±s.e.m., **p<0.01 vs sham, ++p<0.01.
Figure 13:
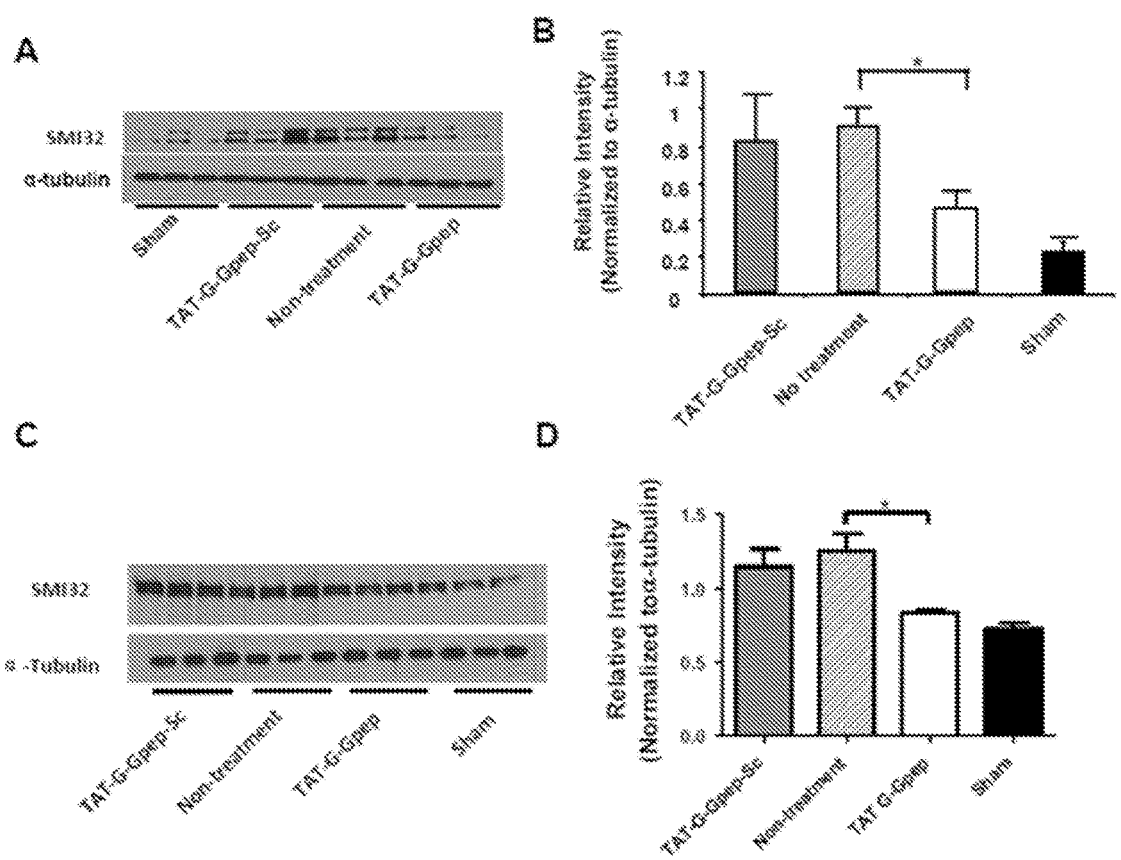
FIG. 13, Panels A-D, represents axonal damage, assessed by Western blot for abnormally dephosphorylated neurofilament H. Panels A, C show Western blot analysis of rat and mouse, respectively, whole spinal cord homogenate visualized by ECL. Panels B, D show densitometric analysis of rat and mouse, respectively, of Western blots of total spinal cord homogenate of three representative animal per group, developed by HRP/DAB. Blots and densitometry were done in triplicate (Sham, TAT-G-Gpep-Sc, no treatment and TAT-G-Gpep). Data represents means±s.e.m. Differences between groups were assessed by Student Newman-Keuls post-hoc one way ANOVA *p<0.05; ns, no significant difference.

IP injection of TAT-G-Gpep also rescues axonal density in the spinal cord of EAE rats/mice compared to EAE rats/mice treated with TAT-G-Gpep-sc. As shown in FIG. 11 (rats) and FIG. 12 (mice), immune-labeled neurofilament-H was significantly increased in the spinal cord of EAE rats/mice treated with TAT-G-Gpep compared to EAE rats/mice treated with TAT-G-Gpep-sc. Furthermore, axonal damage was assessed by Western Blot for abnormally dephosphorylated neurofilament H. TAT-G-Gpep treatment significantly reduced dephosphorylated neurofilament H in EAE rats/mice compared with TAT-G-Gpep-sc (FIG. 13).

Example 4

Figure 14:
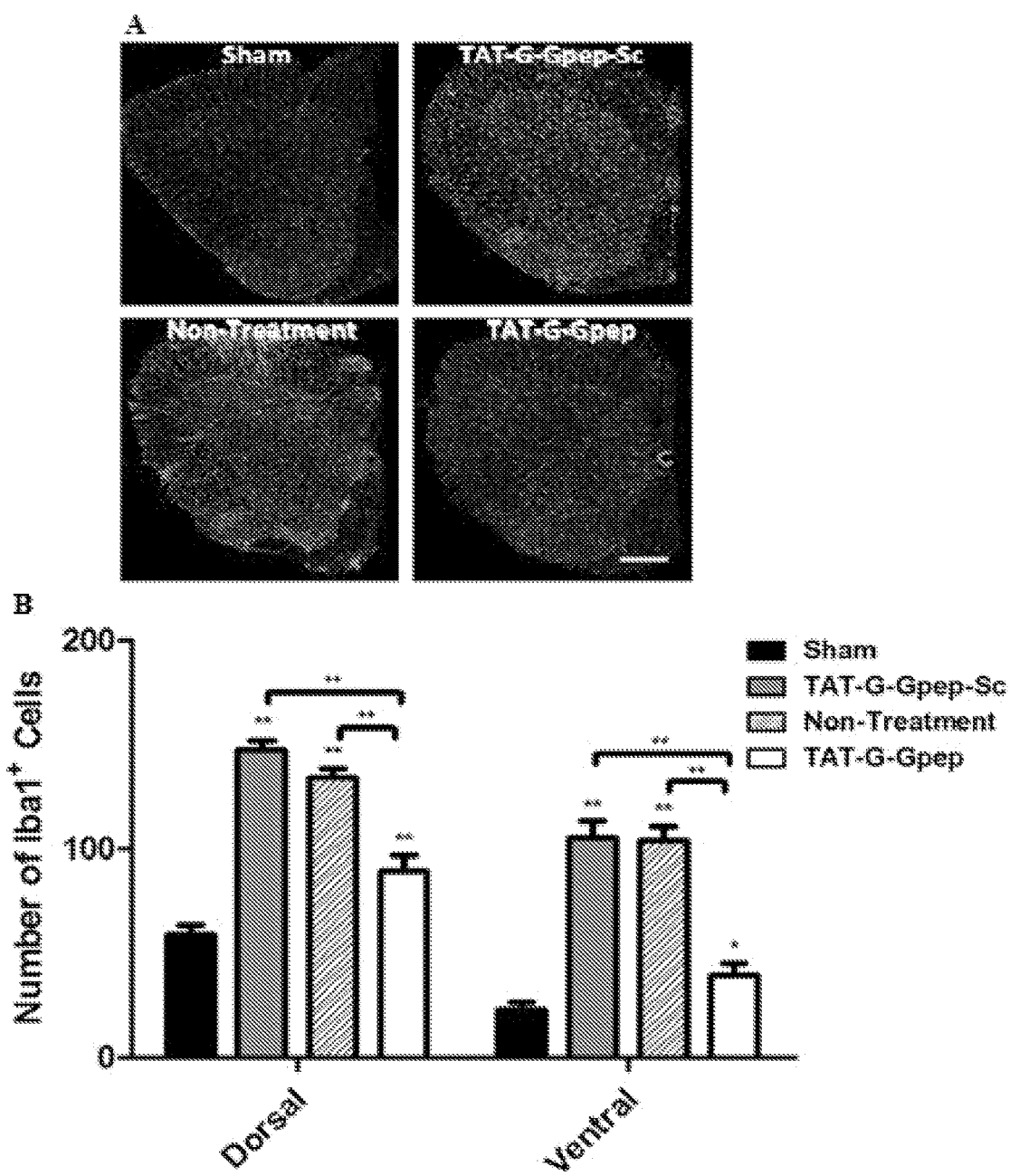
FIG. 14, Panels A-B, shows suppression of macrophages infiltration/microglia activation with TAT-G-Gpep treatment in EAE mouse spinal cord. Panel A, Representative images of Iba1-immunolabeled macrophages/microglia in sham, TAT-G-Gpep-Sc, non-treated and TAT-G-Gpep-treated mouse spinal cords. Scale Bar, 40 μm. Panel B, Quantification of the number of Iba1+ cells in the dorsal and ventral horns revealed significantly more macrophages/microglia residing in scrambled peptide, non-treated and peptide-treated mice when compared to sham. Peptide treatment significantly reduced the amount Iba1+ cells when compared to scrambled peptide or non-treated mice. All data were given as mean±SEM; **p<0.01 vs sham; +p<0.01.
Figure 15:
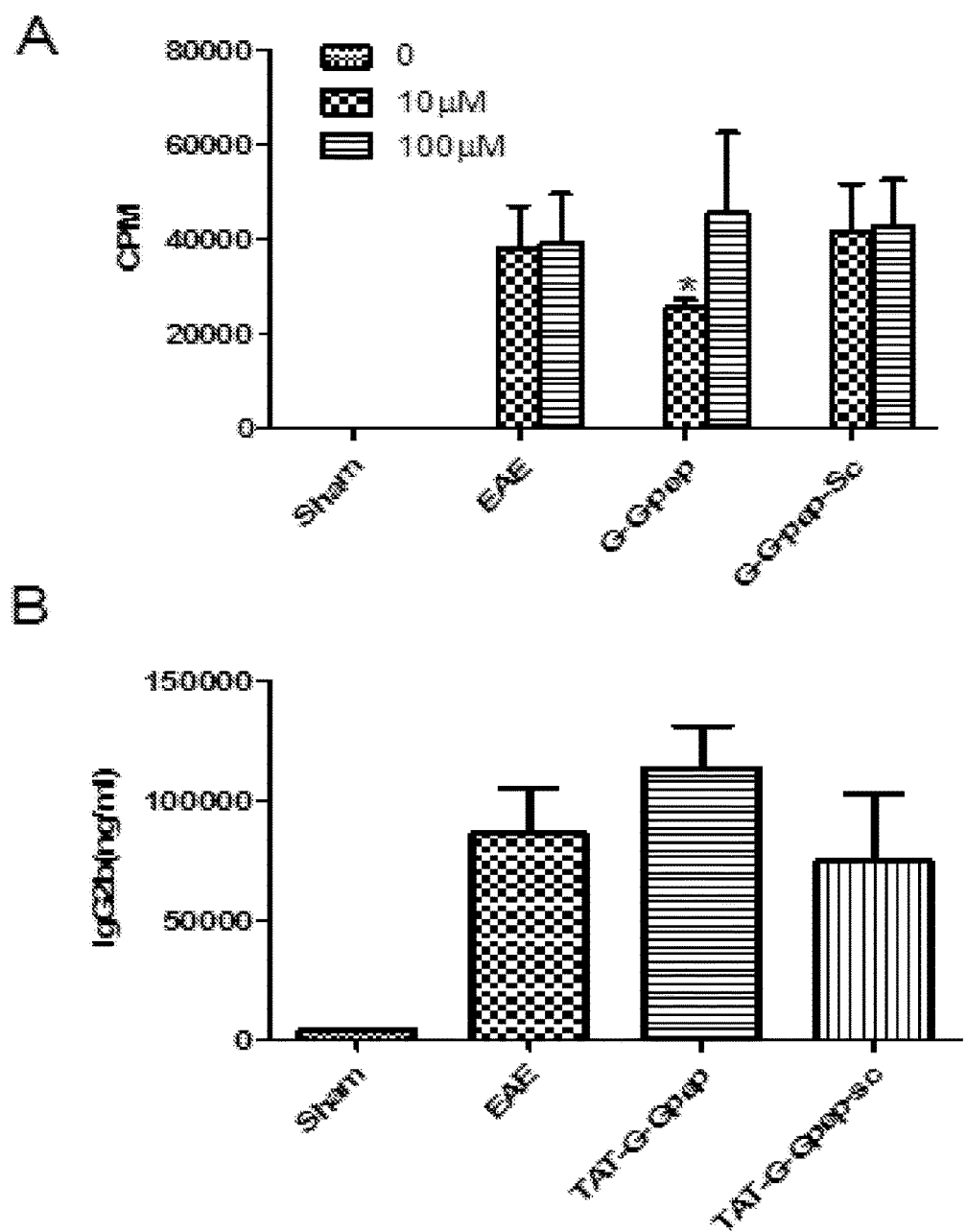
FIG. 15, Panels A-B, show results of tests. Panel A shows splenocytes from different groups that were harvested by the end of the disease course and cultivated in the presence of different concentration of MOG35-55 peptide for T cell proliferation. At low dose of MOG35-55 peptide (10 μM), TAT-G-Gpep could suppress the T cell proliferation but not at high dose (100 μM). Panel B, Serum collected from different groups at the end of the disease course were tested for MOG-specific IgG2b levels. No differences were observed among different treatment groups. *P<0.05.
Figure 18:
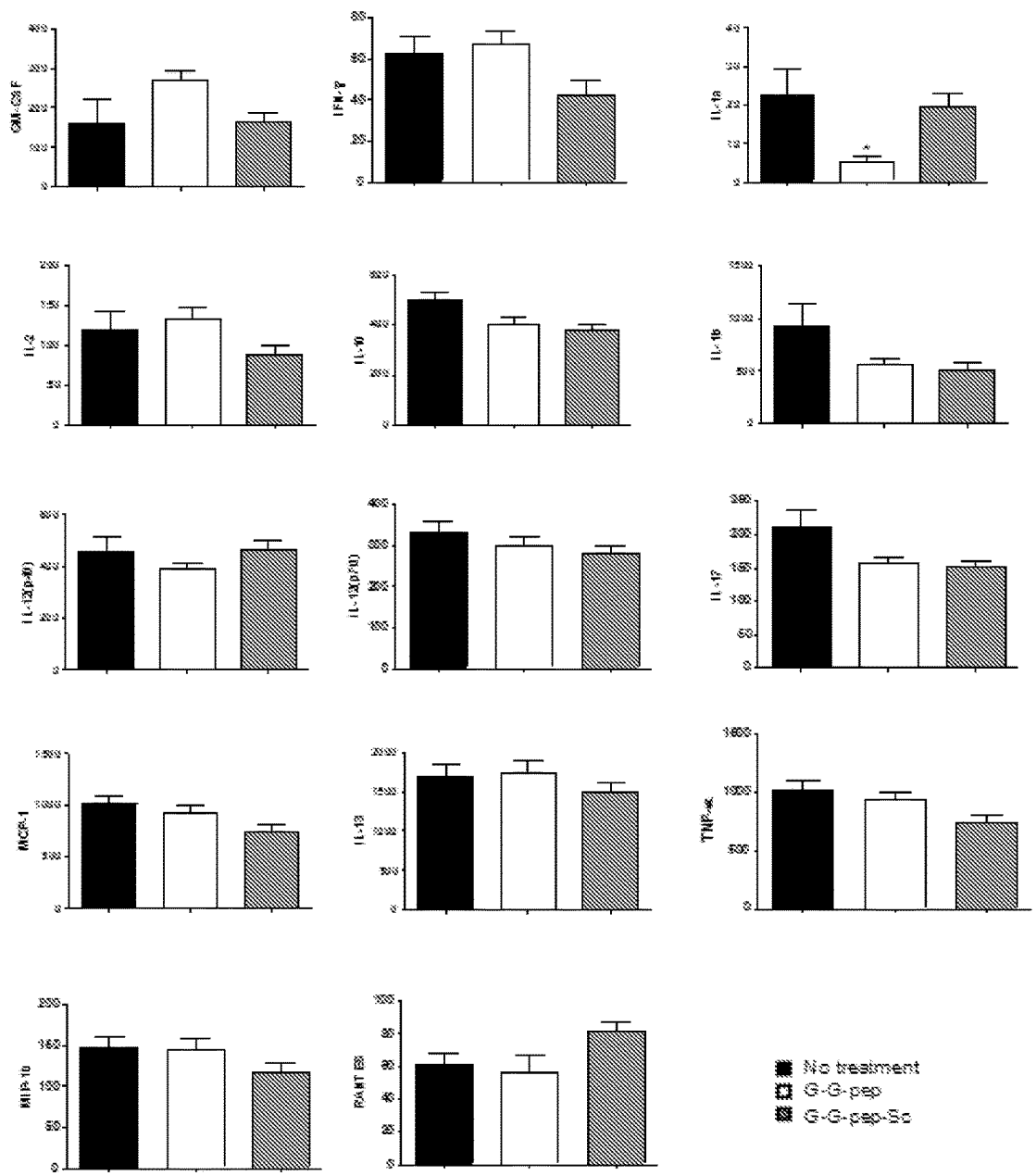
FIG. 18 shows results in bar graph form summarizing the Bioplex array results for cytokine profiles in the blood serum from different groups. No significant changes in the cytokine profile from mice blood serum in different groups were observed.
Figure 19:
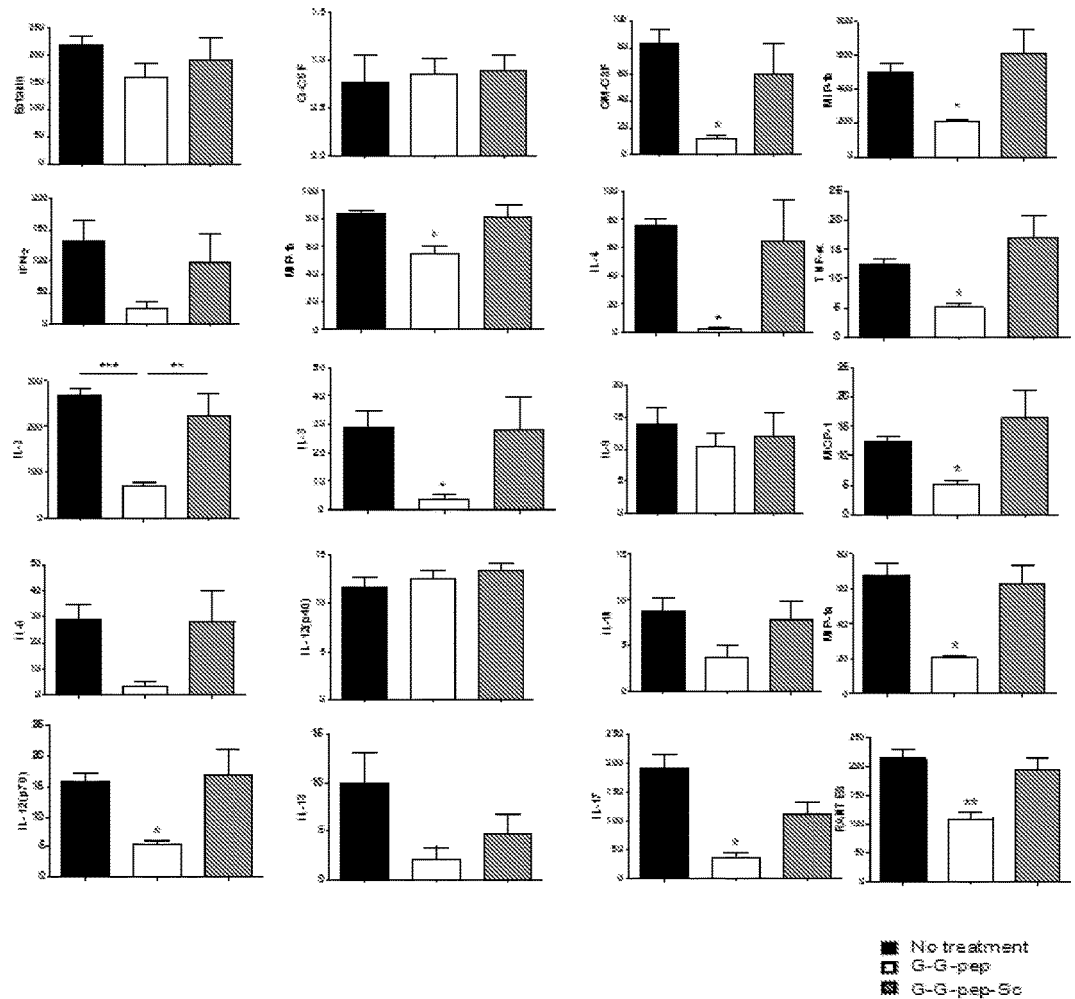
FIG. 19 shows results in bar graph form summarizing the Bioplex results for cytokine profiles in the cultured spleenocytes re-stimulated with MOG35-55 from different groups. For most cytokines, the immunoreactivity of spleenocytes from G-Gpep group is significantly suppressed comparing with the other two groups. (*P<0.05,**P<0.01, comparing with corresponding groups, ANOVA, post hoc SNK test).

Disruption of GluR2-GAPDH Interaction with TAT-G-Gpep Suppressed Macrophage/Microglia Infiltration in EAE Rat/Mice Spinal Cord As MS is closely associated with inflammation and autoimmunity, the TAT-G-Gpep peptide was tested to determine if it affects microglial/macrophage recruitment. As shown in FIG. 14, the number of Iba1+ cells in mouse spinal chord was differentially increased in EAE treatment groups when compared to sham controls and there was a significant difference in Iba1-immunolabeled macrophages/microglia among TAT-G-Gpep-sc, TAT-G-Gpep treated and non-treatment groups. These data suggested that the interfering peptide TAT-G-Gpep has an effect on activation of the immune system in the spinal cord of EAE animals.

Example 5

20 Amino Acid GluR2 N-Terminal Fragment (SEQ ID NO:5) Precipitates GAPDH from Solublized Rat Hippocampal Tissue Production of GST-Fusion Proteins Desired DNA sequences of the GluR2 N-terminus were obtained by polymerase chain reaction. The DNA sequences were digested with BamHI and XhoI enzymes to create sticky ends and subsequently incorporated into GST-plasmids (pGEX4T3) through DNA ligation. Following ligation, transformation with DH5a competent cells was performed to amplify the plasmid content. Subsequently, the plasmids were extracted and subjected to sequence confirmation. Having the desired DNA sequences confirmed, the GST-fusion proteins were expressed through the transformation with another strain of competent cells (i.e. BL21). The GST-fusion proteins were then precipitated and purified through glutathione resin (from Genescript).

Pull-Down Affinity Assay

Rat hippocampus was homogenized in 50 mM Tris-HCl (pH 7.5), 150 mM NaCl, 1% NP-40, 0.5% sodium deoxycholate, 1 mM EDTA, 10% Triton X-100, 1 mM PMSF and protease inhibitor cocktail (Sigma, 5 microl per 100 mg tissue). The hippocampal tissue was further solubilized with 1% Triton X-100 and then centrifuged at 14,000 rpm at 4° C. for 15 mins The solubilized hippocampal tissue (approximately 1 milligram of protein) was incubated with glutathione resin (Genescript) and indicated GST-fusion proteins (approximately 100 μg) at 4° C. overnight and followed by an hour of incubation at room temperature. After the incubation, the samples were washed 4-6 times with 1 mL PBS contained 0.1% Triton X-100. Following the series of washing, 30 μL of glutathione elution buffer was added to elute the proteins from the glutathione beads. The eluates were incubated in sample buffer (final concentration 5% SDS), boiled for 5 minutes and eventually subjected to SDS-PAGE (12% gel). The blots were blocked with 5% non-fat milk dissolved in TBST buffer (10 mM Tris-HCl, 150 mM NaCl and 0.1% Tween) for 1 h at room temperature. Prior to primary antibody incubation, the blots were washed three times with TBST to remove any milk residues. The blots were then incubated with primary antibodies against GAPDH (diluted 1:500, Millipore) at 4° C. overnight. On the next day, GADPH were revealed with peroxidase-conjugated secondary antibodies (Sigma) and enhanced chemiluminescence (GE Healthcare UK Limited).

Figure 20:
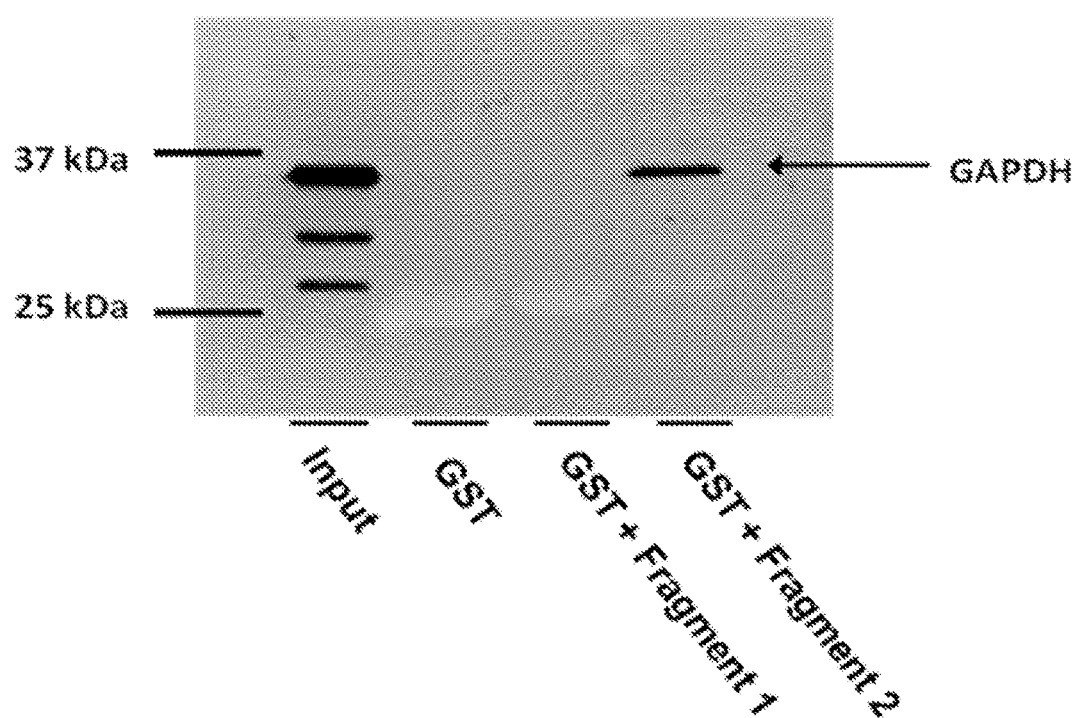
FIG. 20 shows results of the pull-down affinity assay of GluR2-GAPDH Interaction. Three different fusion proteins were employed to precipitate GAPDH from hippocampal tissue homogenate. One of the fusion proteins was glutathione S-transferase alone (GST), which served as the negative control in this experiment. The other two fusion proteins were derived from two different fragments of the GluR2 N-terminus. Fragment 1 contained Tyr142-Leu161 amino acid residues of the GluR2 N-terminus (SEQ ID NO:7), while fragment 2 encoded an amino sequence of Asp153-Lys172 (SEQ ID NO:5). Only the GST fusion protein containing fragment 2 was able to precipitate GAPDH (weight approximately 36 kDa) proteins from solubilized rat hippocampal tissue among all three fusion proteins. For each of the pull-down assays presented above, a lane of pure rat hippocampal tissue homogeneate (70-100 μg) was included as positive control.

Three different GST-fusion proteins were tested in this pull-down affinity assay. They were respectively GST alone, GST-Fragment 1 (wherein fragment 1 is Tyr142-Leu161 of GluR2 N-terminus; YYQWDKFAYLYDSDRGLSTL (SEQ ID NO:7)) and GST-Fragment 2 (wherein fragment 2 is Asp153-Lys172 of GluR2 N-terminus; DSDRGLSTLQAV-LDSAAEKK (SEQ ID NO:5)) fusion proteins. As observed in FIG. 20, neither the GST alone nor the GST-fusion protein containing fragment 1 (Tyr142-Leu161 (SEQ ID NO:7)) sufficed to "pull down" GAPDH from the solubilized hippocampal tissue. On the other hand, the GST-fusion protein containing fragment 2 (Asp153-Lys172 (SEQ ID NO:5)) of the GluR2 N-terminus was able to precipitate GAPDH, which weighs approximately 36 kDa. It is worth noting that the input lane was designated as the positive control and its GAPDH band perfectly aligned with the one in the GST-fragment 2 lane, further confirming the successful precipitation by GST-fragment2 fusion protein. Based on this finding, but without wishing to be bound by any particular theory or limiting in any manner, it is clear that the 20 amino acid sequence of fragment 2 was important in facilitating the protein interaction between GluR2 and GAPDH.

The present invention has been described with regard to one or more embodiments. However, it will be apparent to persons skilled in the art that a number of variations and modifications can be made without departing from the scope of the invention as defined in the claims.

The disclosure provided contains statements that are based on experimental results provided herein. The disclosure may also comprise statements that are forward looking and/or predicted based on the results presented herein and should not be taken as promises of the invention. Finally, the application comprises disclosure for the purpose of providing literal support for claim amendments in response to unknown prior art.

All citations are herein incorporated by reference.

The invention claimed is:

1. A method for supressing macrophage infiltration, microglia activation or infiltration of leukocytes in the central nervous system (CNS) of a subject that exhibits multiple sclerosis-like symptoms of axonal damage, oligodendrocyte death, demyelination or a combination thereof comprising administering a polypeptide (a) comprising Asp153-Lys172 of the GluR2 N-terminus (DSDRGLSTLQAVLDSAAEKK (SEQ ID NO:5)) and wherein the polypeptide does not comprise SEQ ID NO:1 or (b) of between 31 and 200 amino acids comprising a GluR2 NT1-3-2 (Y142-K172) amino acid sequence defined by SEQ ID NO:1 to the subject to suppress macrophage infiltration, microglia activation or infiltration of leukocytes in the CNS of the subject.

2. The method of claim 1, wherein said polypeptide consists of SEQ ID NO:1 or SEQ ID NO:5.

3. The method of claim 1, wherein said polypeptide is covalently attached to a heterologous polypeptide, to form a fusion protein.

4. The method of claim 3, wherein said fusion protein comprises a protein transduction domain.

5. The method of claim 3, wherein said heterologous polypeptide does not encompass a GluR2 subunit sequence.

6. The method of claim 1, wherein said polypeptide is attached covalently or non-covalently to a non-protein substrate, non-protein molecule, non-protein macromolecule, or any combination thereof.

7. The method of claim 6, wherein the polypeptide, non-protein substrate, non-protein molecule, non-protein macromolecule, or any combination thereof is labelled.

8. The method of claim 1, wherein the subject is a human.

9. The method of claim 1, wherein the polypeptide is administered in the form of a composition comprising the polypeptide and a pharmaceutically acceptable carrier, diluent, or excipient.

10. The method of claim 1 wherein the subject exhibits demyelination.

11. A method for supressing macrophage infiltration, microglia activation or infiltration of leukocytes in the central nervous system (CNS) of a subject that exhibits multiple sclerosis-like symptoms of axonal damage, oligodendrocyte death, demyelination or a combination thereof comprising administering a composition comprising a polypeptide (a) comprising Asp153-Lys172 of the GluR2 N-terminus (DSDRGLSTLQAVLDSAAEKK (SEQ ID NO:5)) and wherein the polypeptide does not comprise SEQ ID NO:1 or (b) of between 31 and 200 amino acids comprising a GluR2 NT1-3-2 (Y142-K172) amino acid sequence defined by SEQ ID NO:1 to the subject to suppress macrophage infiltration, microglia activation or infiltration of leukocytes in the CNS of the subject.

12. The method of claim 11, wherein said polypeptide consists of SEQ ID NO:1 or SEQ ID NO:5.

13. The method of claim 11, wherein said polypeptide is covalently attached to a heterologous polypeptide, to form a fusion protein.

14. The method of claim 13, wherein said fusion protein comprises a protein transduction domain.

15. The method of claim 13, wherein said heterologous polypeptide does not encompass a GluR2 subunit sequence.

16. The method of claim 11, wherein said polypeptide is attached covalently or non-covalently to a non-protein substrate, non-protein molecule, non-protein macromolecule, or any combination thereof.

17. The method of claim 16, wherein the polypeptide, non-protein substrate, non-protein molecule, non-protein macromolecule, or any combination thereof is labelled.

18. The method of claim 16, wherein said polypeptide consists of SEQ ID NO:1 or SEQ ID NO:5.

19. The method of claim 11, wherein the subject is a human.

20. The method of claim 11, wherein the composition further comprises a pharmaceutically acceptable carrier, diluent, or excipient.

21. A method for supressing macrophage infiltration, microglia activation or infiltration of leukocytes in the central nervous system (CNS) of a subject that exhibits multiple sclerosis-like symptoms of axonal damage, oligodendrocyte death, demyelination or a combination thereof comprising administering a polypeptide (a) comprising Asp153-Lys172 of the GluR2 N-terminus (DSDRGLSTLQAVLDSAAEKK (SEQ ID NO:5)) and wherein the polypeptide does not comprise SEQ ID NO:1 or (b) of between 31 and 200 amino acids comprising a GluR2 NT1-3-2 (Y142-K172) amino acid sequence defined by SEQ ID NO:1 to the subject to suppress macrophage infiltration, microglia activation or infiltration of leukocytes in the CNS of the subject, and wherein the method increases neuronal survival in the subject.

* * * * *